United States Patent
Enck et al.

(10) Patent No.: US 9,646,258 B2
(45) Date of Patent: May 9, 2017

(54) TECHNIQUES TO PROVIDE REAL-TIME PROCESSING ENHANCEMENTS AND MODELING FOR DATA ANOMALY DETECTION PERTAINING TO MEDICAL EVENTS USING DECISION TREES

(71) Applicant: SAS Institute Inc., Cary, NC (US)

(72) Inventors: Steven William Enck, Apex, NC (US); Emily Chapman-McQuiston, Cary, NC (US); Daniel Kelly, Raleigh, NC (US)

(73) Assignee: SAS Institute Inc., Cary, NC (US)

( * ) Notice: Subject to any disclaimer, the term of this patent is extended or adjusted under 35 U.S.C. 154(b) by 0 days.

(21) Appl. No.: 15/274,589

(22) Filed: Sep. 23, 2016

(65) Prior Publication Data

US 2017/0091642 A1   Mar. 30, 2017

Related U.S. Application Data

(60) Provisional application No. 62/232,006, filed on Sep. 24, 2015.

(51) Int. Cl.
| | | |
|---|---|---|
| *G06F 15/18* | (2006.01) | |
| *G06N 7/00* | (2006.01) | |
| *G06F 17/30* | (2006.01) | |
| *G06F 19/00* | (2011.01) | |

(52) U.S. Cl.
CPC ....... *G06N 7/005* (2013.01); *G06F 17/30309* (2013.01); *G06F 17/30961* (2013.01); *G06F 19/3437* (2013.01)

(58) Field of Classification Search
CPC ........................... G06F 19/345; G06F 19/3437

USPC ............................................. 706/12, 45, 62
See application file for complete search history.

(56) References Cited

U.S. PATENT DOCUMENTS

| | | | |
|---|---|---|---|
| 5,627,908 A * | 5/1997 | Lee .................... | G01N 15/1475 |
| | | | 382/128 |
| 6,879,959 B1 | 4/2005 | Chapman et al. | |
| 8,015,136 B1 * | 9/2011 | Baker .................. | G06F 19/322 |
| | | | 706/45 |

(Continued)

OTHER PUBLICATIONS

"Predictive Modeling Analysis of Medicare Claims", MLN Matters, Department of Health and Human Services Centers for Medicare & Medicaid Services, 2010, 3 pages.

*Primary Examiner* — David Vincent

(57) ABSTRACT

Embodiments are generated directed to method, medium, and system including processing circuitry to generate records including randomly selected events for each of one or more subjects having one or more of the same category parameters as a subject of a particular event. The processing circuitry may also present, on a display device, a computer-generated model based on the records, the model having a decision tree data structure having decision tree nodes corresponding with historical events from the records, each of the decision tree nodes having an indication of a likelihood of occurrence for the particular event based on whether a corresponding history event of the decision tree node occurred or did not occur within a specific time period. Embodiments of the real-time distributed nature of the systems and processing discussed herein can solve big data analytics processing problems and facilitate data anomaly detection.

30 Claims, 23 Drawing Sheets

(56) References Cited

U.S. PATENT DOCUMENTS

| | | | |
|---|---|---|---|
| 2004/0230397 A1* | 11/2004 | Chadwick | G06Q 10/10 702/181 |
| 2007/0244724 A1 | 10/2007 | Pendergast et al. | |
| 2009/0210252 A1 | 8/2009 | Silver | |
| 2011/0195064 A1* | 8/2011 | Rimsza | G01N 33/57407 424/133.1 |
| 2015/0046181 A1 | 2/2015 | Adjaoute | |

* cited by examiner

TECHNIQUES TO PROVIDE REAL-TIME PROCESSING ENHANCEMENTS AND MODELING FOR DATA ANOMALY DETECTION PERTAINING TO MEDICAL EVENTS USING DECISION TREES

RELATED APPLICATION

This application claims the benefit of priority of 35 U.S.C. §119(e) to U.S. Provisional Patent Application Ser. No. 62/232,006, filed on Sep. 24, 2015, which is incorporated by reference.

BRIEF DESCRIPTION OF THE DRAWINGS

Embodiments of this disclosure are illustrated by way of example and not by way of limitation, in the figures of the accompanying drawings in which like reference numerals refer to similar elements.

DETAILED DESCRIPTION

Figure 1:
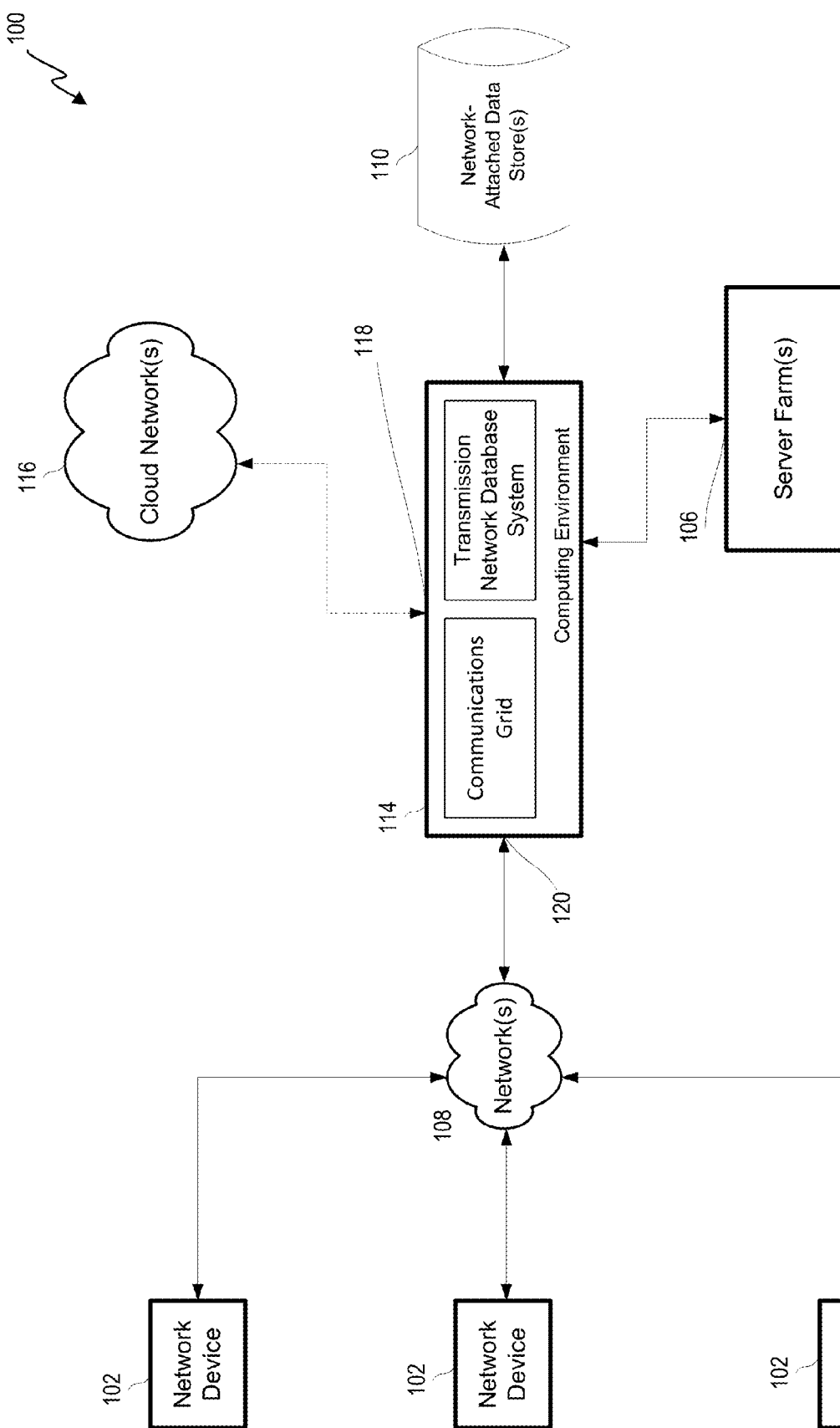
FIG. 1 illustrates a block diagram that provides an illustration of the hardware components of a computing system, according to some embodiments of the present technology.

With general reference to notations and nomenclature used herein, portions of the detailed description that follows may be presented in terms of program procedures executed by a processor component of a machine or of multiple networked machines. These procedural descriptions and representations are used by those skilled in the art to most effectively convey the substance of their work to others skilled in the art. A procedure is here, and generally, conceived to be a self-consistent sequence of operations leading to a desired result. These operations are those requiring physical manipulations of physical quantities. Usually, though not necessarily, these quantities take the form of electrical, magnetic or optical communications capable of being stored, transferred, combined, compared, and otherwise manipulated. It proves convenient at times, principally for reasons of common usage, to refer to what is communicated as bits, values, elements, symbols, characters, terms, numbers, or the like. It should be noted, however, that all of these and similar terms are to be associated with the appropriate physical quantities and are merely convenient labels applied to those quantities.

Further, these manipulations are often referred to in terms, such as adding or comparing, which are commonly associated with mental operations performed by a human operator. However, no such capability of a human operator is necessary, or desirable in most cases, in any of the operations described herein that form part of one or more embodiments. Rather, these operations are machine operations. Useful machines for performing operations of various embodiments include machines selectively activated or configured by a routine stored within that is written in accordance with the teachings herein, and/or include apparatus specially constructed for the required purpose. Various embodiments also relate to apparatus or systems for performing these operations. These apparatus may be specially constructed for the required purpose or may include a general purpose computer. The required structure for a variety of these machines will appear from the description given.

Reference is now made to the drawings, wherein like reference numerals are used to refer to like elements throughout. In the following description, for purposes of explanation, numerous specific details are set forth in order to provide a thorough understanding thereof. It may be evident, however, that the novel embodiments can be practiced without these specific details. In other instances, well known structures and devices are shown in block diagram form in order to facilitate a description thereof. The intention is to cover all modifications, equivalents, and alternatives within the scope of the claims.

Systems depicted in some of the figures may be provided in various configurations. In some embodiments, the systems may be configured as a distributed system where one or more components of the system are distributed across one or more networks in a cloud computing system.

FIG. 1 is a block diagram that provides an illustration of the hardware components of a data transmission network 100, according to embodiments of the present technology. Data transmission network 100 is a specialized computer system that may be used for processing large amounts of data (e.g., event history information, codes, etc.) where a large number of computer processing cycles are required.

Data transmission network 100 may also include computing environment 114. Computing environment 114 may be a specialized computer or other machine that processes the data received within the data transmission network 100. Data transmission network 100 also includes one or more network devices 102. Network devices 102 may include client devices that attempt to communicate with computing environment 114. For example, network devices 102 may send data to the computing environment 114 to be processed, may send signals to the computing environment 114 to control different aspects of the computing environment or the data it is processing, among other reasons. Network devices 102 may interact with the computing environment 114 through a number of ways, such as, for example, over one or more networks 108. As shown in FIG. 1, computing environment 114 may include one or more other systems. For example, computing environment 114 may include a database system 118 and/or a communications grid 120.

Figure 8:
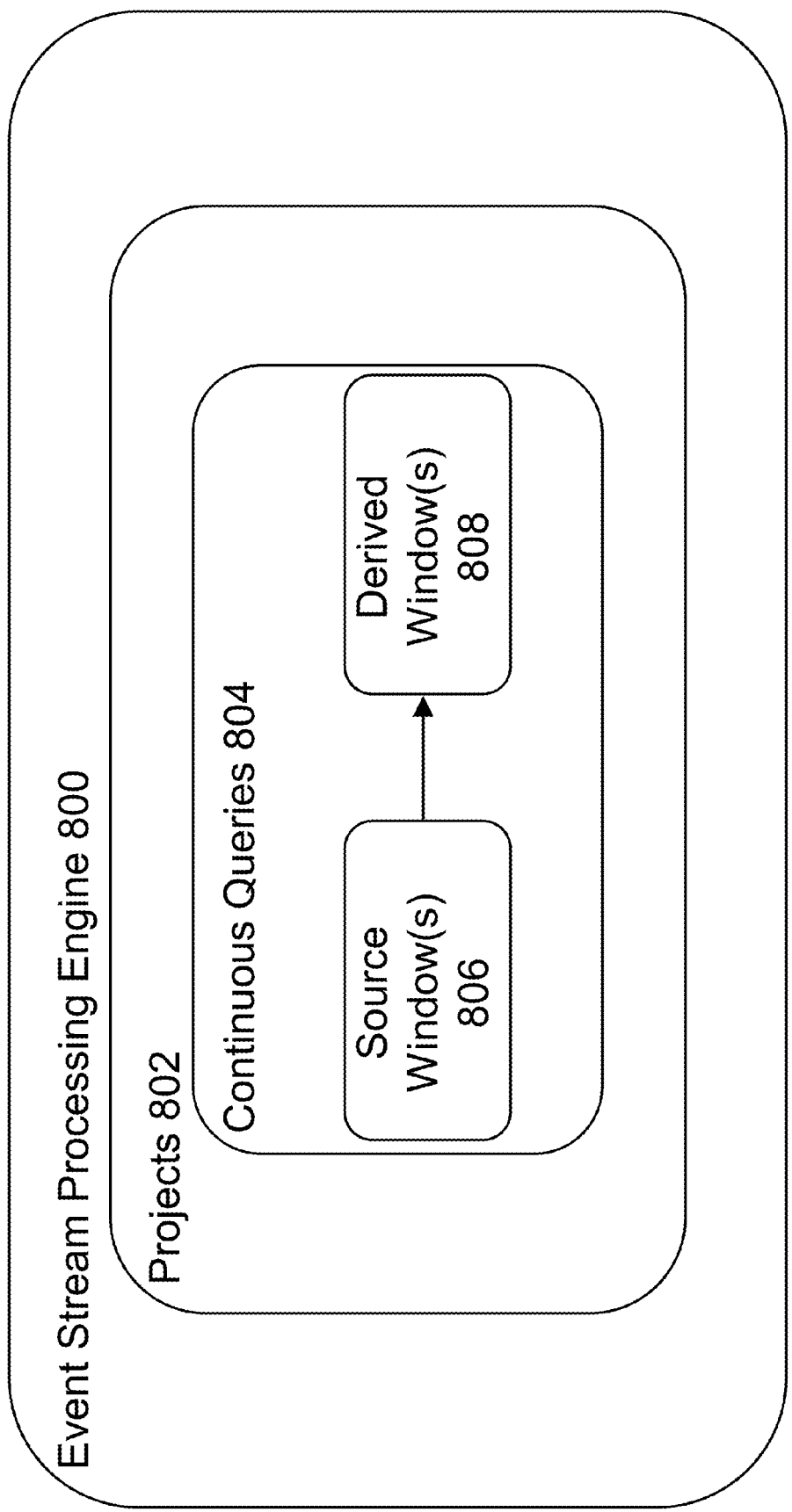
FIG. 8 illustrates a block diagram including components of an Event Stream Processing Engine (ESPE), according to some embodiments of the present technology.
Figure 9:
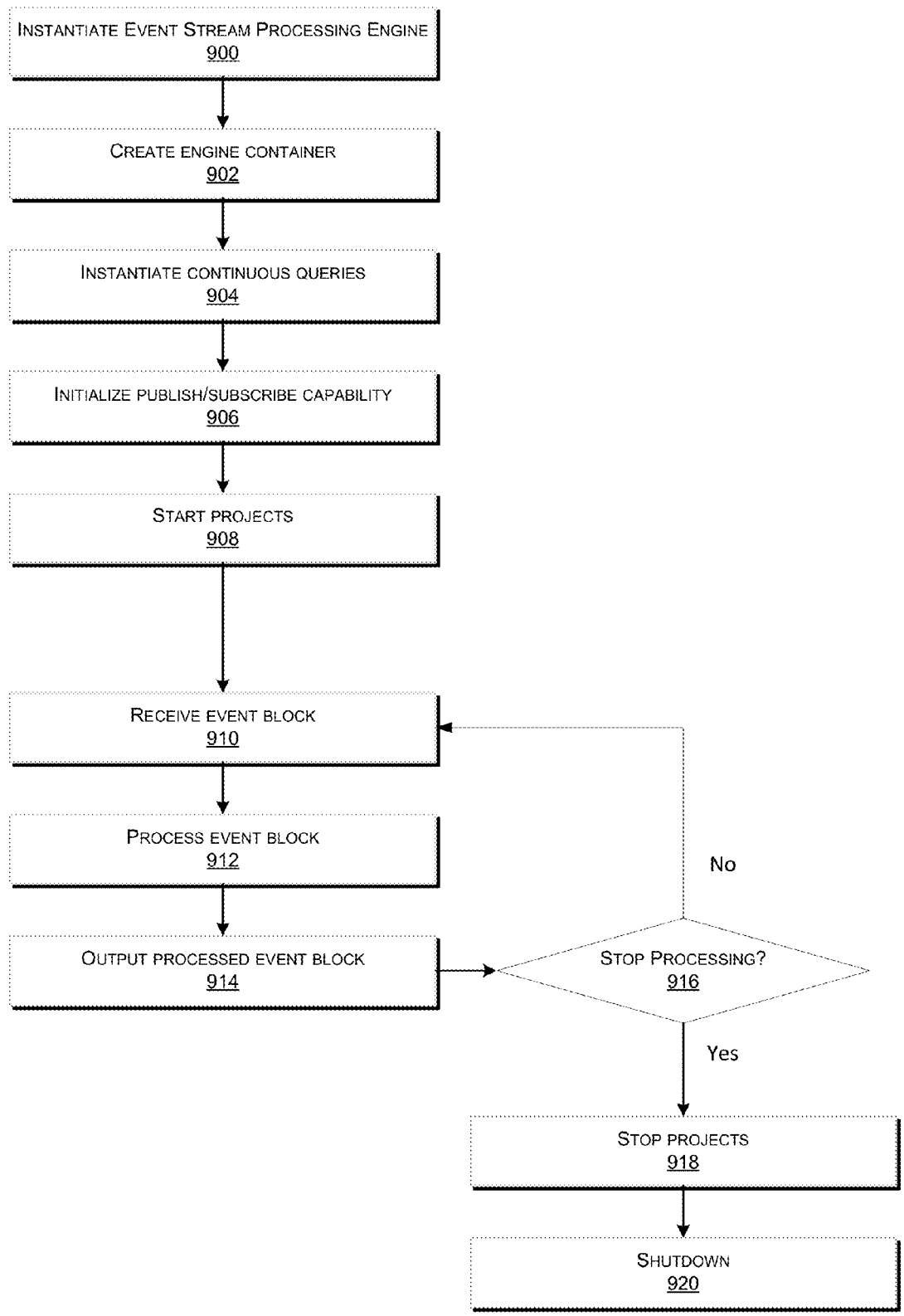
FIG. 9 illustrates a flow chart showing an example process including operations performed by an event stream processing engine, according to some embodiments of the present technology.
Figure 10:
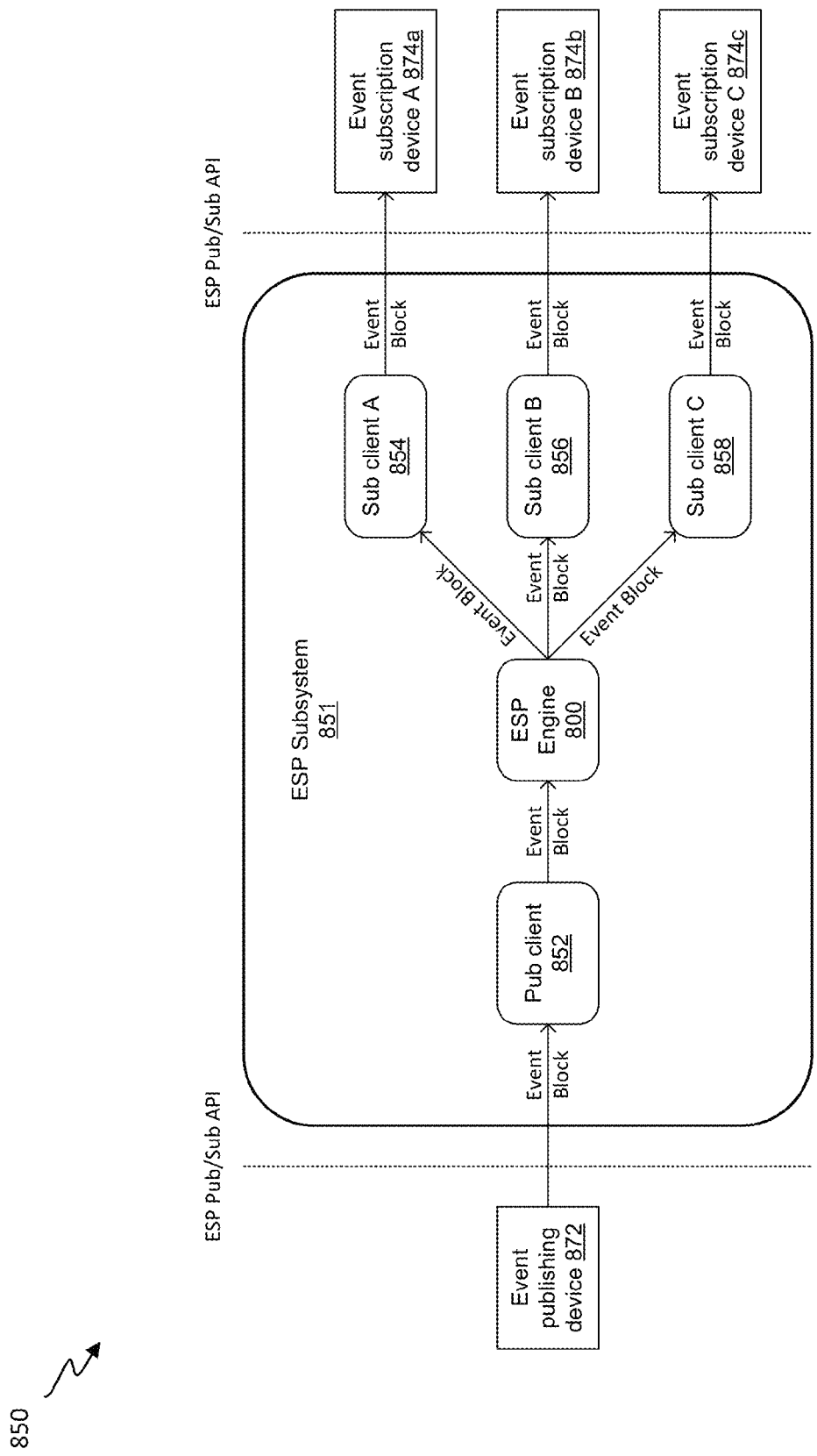
FIG. 10 illustrates an ESP system interfacing between a publishing device and multiple event subscribing devices, according to embodiments of the present technology.

In other embodiments, network devices may provide a large amount of data, either all at once or streaming over a period of time (e.g., using event stream processing (ESP), described further with respect to FIGS. 8-10), to the computing environment 114 via networks 108. For example, network devices 102 may include network computers, sensors, databases, or other devices that may transmit or otherwise provide data to computing environment 114. For example, network devices may include local area network devices, such as routers, hubs, switches, or other computer networking devices. These devices may provide a variety of stored or generated data, such as network data or data specific to the network devices themselves. Network devices may also include sensors that monitor their environment or other devices to collect data regarding that environment or those devices, and such network devices may provide data they collect over time. Network devices may also include devices within the internet of things, such as devices within a home automation network. Some of these devices may be referred to as edge devices, and may involve edge computing circuitry. Data may be transmitted by network devices directly to computing environment 114 or to network-attached data stores, such as network-attached data stores 110 for storage so that the data may be retrieved later by the computing environment 114 or other portions of data transmission network 100.

Data transmission network 100 may also include one or more network-attached data stores 110. Network-attached data stores 110 are used to store data (e.g., event history information, codes, subject data, etc.) to be processed by the computing environment 114 as well as any intermediate or final data generated by the computing system in non-volatile memory. However in certain embodiments, the configuration of the computing environment 114 allows its operations to be performed such that intermediate and final data results can be stored solely in volatile memory (e.g., RAM), without a requirement that intermediate or final data results be stored to non-volatile types of memory (e.g., disk). This can be useful in certain situations, such as when the computing environment 114 receives ad hoc queries from a user and when responses, which are generated by processing large amounts of data, need to be generated on-the-fly. In this non-limiting situation, the computing environment 114 may be configured to retain the processed information within memory so that responses can be generated for the user at different levels of detail as well as allow a user to interactively query against this information.

Network-attached data stores may store a variety of different types of data organized in a variety of different ways and from a variety of different sources. For example, network-attached data storage may include storage other than primary storage located within computing environment 114 that is directly accessible by processors located therein. Network-attached data storage may include secondary, tertiary or auxiliary storage, such as large hard drives, servers, virtual memory, among other types. Storage devices may include portable or non-portable storage devices, optical storage devices, and various other mediums capable of storing, containing data. A machine-readable storage medium or computer-readable storage medium may include a non-transitory medium in which data can be stored and that does not include carrier waves and/or transitory electronic signals. Examples of a non-transitory medium may include, for example, a magnetic disk or tape, optical storage media such as compact disk or digital versatile disk, flash memory, memory or memory devices. A computer-program product may include code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, among others. Furthermore, the data stores may hold a variety of different types of data. For example, network-attached data stores 110 may hold unstructured (e.g., raw) data, such as manufacturing data (e.g., a database containing records identifying products being manufactured with parameter data for each product, such as colors and models) or product sales databases (e.g., a database containing individual data records identifying details of individual product sales).

The unstructured data may be presented to the computing environment 114 in different forms such as a flat file or a conglomerate of data records, and may have data values and accompanying time stamps. The computing environment 114 may be used to analyze the unstructured data in a variety of ways to determine the best way to structure (e.g., hierarchically) that data, such that the structured data is tailored to a type of further analysis that a user wishes to perform on the data. For example, after being processed, the unstructured time stamped data may be aggregated by time (e.g., into daily time period units) to generate time series data and/or structured hierarchically according to one or more dimensions (e.g., parameters, attributes, and/or variables). For example, data may be stored in a hierarchical data structure, such as a ROLAP OR MOLAP database, or may be stored in another tabular form, such as in a flat-hierarchy form.

Data transmission network 100 may also include one or more server farms 106. Computing environment 114 may route select communications or data to the one or more sever farms 106 or one or more servers within the server farms. Server farms 106 can be configured to provide information in a predetermined manner. For example, server farms 106 may access data to transmit in response to a communication. Server farms 106 may be separately housed from each other device within data transmission network 100, such as computing environment 114, and/or may be part of a device or system.

Server farms 106 may host a variety of different types of data processing as part of data transmission network 100. Server farms 106 may receive a variety of different data from network devices, from computing environment 114, from cloud network 116, or from other sources. The data may have been obtained or collected from one or more sensors, as inputs from a control database, or may have been received as inputs from an external system or device. Server farms 106 may assist in processing the data by turning raw data into processed data based on one or more rules implemented by the server farms. For example, sensor data may be analyzed to determine changes in an environment over time or in real-time.

Data transmission network 100 may also include one or more cloud networks 116. Cloud network 116 may include a cloud infrastructure system that provides cloud services. In certain embodiments, services provided by the cloud network 116 may include a host of services that are made available to users of the cloud infrastructure system on demand. Cloud network 116 is shown in FIG. 1 as being connected to computing environment 114 (and therefore having computing environment 114 as its client or user), but cloud network 116 may be connected to or utilized by any of the devices in FIG. 1. Services provided by the cloud network can dynamically scale to meet the needs of its users. The cloud network 116 may comprise one or more computers, servers, and/or systems. In some embodiments, the computers, servers, and/or systems that make up the cloud network 116 are different from the user's own on-premises computers, servers, and/or systems. For example, the cloud network 116 may host an application, and a user may, via a communication network such as the Internet, on demand, order and use the application.

While each device, server and system in FIG. 1 is shown as a single device, it will be appreciated that multiple devices may instead be used. For example, a set of network devices can be used to transmit various communications from a single user, or remote server 140 may include a server stack. As another example, data may be processed as part of computing environment 114.

Each communication within data transmission network 100 (e.g., between client devices, between a device and connection management system 150, between servers 106 and computing environment 114 or between a server and a device) may occur over one or more networks 108. Networks 108 may include one or more of a variety of different types of networks, including a wireless network, a wired network, or a combination of a wired and wireless network. Examples of suitable networks include the Internet, a personal area network, a local area network (LAN), a wide area network (WAN), or a wireless local area network (WLAN). A wireless network may include a wireless interface or combination of wireless interfaces. As an example, a network in the one or more networks 108 may include a short-range communication channel, such as a Bluetooth or a Bluetooth Low Energy channel. A wired network may include a wired interface. The wired and/or wireless networks may be implemented using routers, access points, bridges, gateways, or the like, to connect devices in the network 114, as will be further described with respect to FIG. 2. The one or more networks 108 can be incorporated entirely within or can include an intranet, an extranet, or a combination thereof. In one embodiment, communications between two or more systems and/or devices can be achieved by a secure communications protocol, such as secure sockets layer (SSL) or transport layer security (TLS). In addition, data and/or transactional details may be encrypted.

Some aspects may utilize the Internet of Things (IoT), where things (e.g., machines, devices, phones, sensors) can be connected to networks and the data from these things can be collected and processed within the things and/or external to the things. For example, the IoT can include sensors in many different devices, and high value analytics can be applied to identify hidden relationships and drive increased efficiencies. This can apply to both big data analytics and real-time (e.g., ESP) analytics. This will be described further below with respect to FIG. 2.

As noted, computing environment 114 may include a communications grid 120 and a transmission network database system 118. Communications grid 120 may be a grid-based computing system for processing large amounts of data. The transmission network database system 118 may be for managing, storing, and retrieving large amounts of data that are distributed to and stored in the one or more network-attached data stores 110 or other data stores that reside at different locations within the transmission network database system 118. The compute nodes in the grid-based computing system 120 and the transmission network database system 118 may share the same processor hardware, such as processors that are located within computing environment 114.

Figure 2:
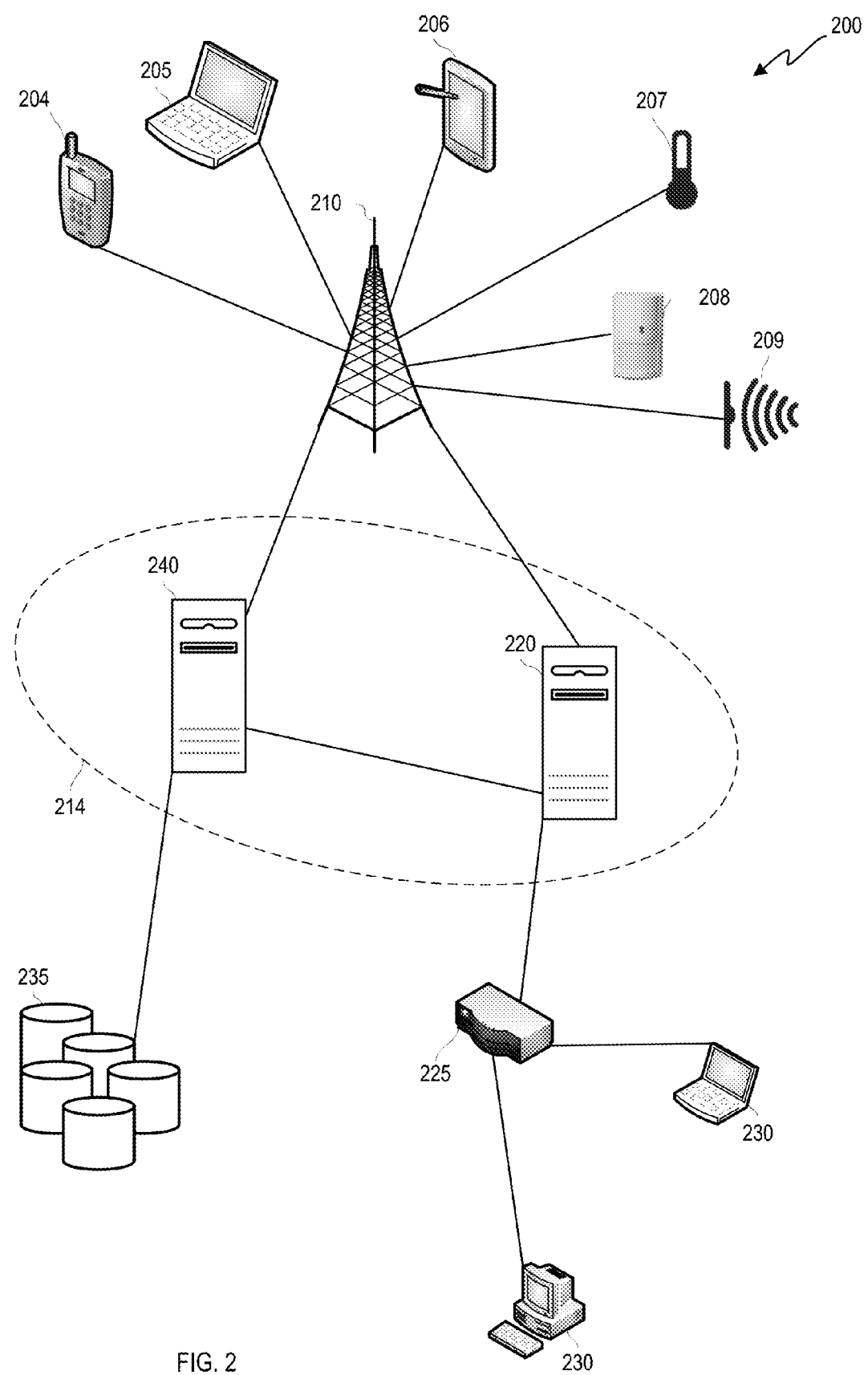
FIG. 2 illustrates an example network including an example set of devices communicating with each other over an exchange system and via a network, according to some embodiments of the present technology.

FIG. 2 illustrates an example network including an example set of devices communicating with each other over an exchange system and via a network, according to embodiments of the present technology. As noted, each communication within data transmission network 100 may occur over one or more networks. System 200 includes a network device 204 configured to communicate with a variety of types of client devices, for example client devices 230, over a variety of types of communication channels.

As shown in FIG. 2, network device 204 can transmit a communication over a network (e.g., a cellular network via a base station 210). The communication can be routed to another network device, such as network devices 205-209, via base station 210. The communication can also be routed to computing environment 214 via base station 210. For example, network device 204 may collect data either from its surrounding environment or from other network devices (such as network devices 205-209) and transmit that data to computing environment 214.

Although network devices 204-209 are shown in FIG. 2 as a mobile phone, laptop computer, tablet computer, temperature sensor, motion sensor, and audio sensor respectively, the network devices may be or include sensors that are sensitive to detecting aspects of their environment. For example, the network devices may include sensors such as water sensors, power sensors, electrical current sensors, chemical sensors, optical sensors, pressure sensors, geographic or position sensors (e.g., GPS), velocity sensors, acceleration sensors, flow rate sensors, among others. Examples of characteristics that may be sensed include force, torque, load, strain, position, temperature, air pressure, fluid flow, chemical properties, resistance, electromagnetic fields, radiation, irradiance, proximity, acoustics, moisture, distance, speed, vibrations, acceleration, electrical potential, electrical current, among others. The sensors may be mounted to various components used as part of a variety of different types of systems (e.g., an oil drilling operation).

The network devices may detect and record data related to the environment that it monitors, and transmit that data to computing environment 214.

As noted, one type of system that may include various sensors that collect data to be processed and/or transmitted to a computing environment according to certain embodiments includes an oil drilling system. For example, the one or more drilling operation sensors may include surface sensors that measure a hook load, a fluid rate, a temperature and a density in and out of the wellbore, a standpipe pressure, a surface torque, a rotation speed of a drill pipe, a rate of penetration, a mechanical specific energy, etc. and downhole sensors that measure a rotation speed of a bit, fluid densities, downhole torque, downhole vibration (axial, tangential, lateral), a weight applied at a drill bit, an annular pressure, a differential pressure, an azimuth, an inclination, a dog leg severity, a measured depth, a vertical depth, a downhole temperature, etc. Besides the raw data collected directly by the sensors, other data may include parameters either developed by the sensors or assigned to the system by a client or other controlling device. For example, one or more drilling operation control parameters may control settings such as a mud motor speed to flow ratio, a bit diameter, a predicted formation top, seismic data, weather data, etc. Other data may be generated using physical models such as an earth model, a weather model, a seismic model, a bottom hole assembly model, a well plan model, an annular friction model, etc. In addition to sensor and control settings, predicted outputs, of for example, the rate of penetration, mechanical specific energy, hook load, flow in fluid rate, flow out fluid rate, pump pressure, surface torque, rotation speed of the drill pipe, annular pressure, annular friction pressure, annular temperature, equivalent circulating density, etc. may also be stored in the data warehouse.

In another example, another type of system that may include various sensors that collect data to be processed and/or transmitted to a computing environment according to certain embodiments includes a home automation or similar automated network in a different environment, such as an office space, school, public space, sports venue, or a variety of other locations. Network devices in such an automated network may include network devices that allow a user to access, control, and/or configure various home appliances located within the user's home (e.g., a television, radio, light, fan, humidifier, sensor, microwave, iron, and/or the like), or outside of the user's home (e.g., exterior motion sensors, exterior lighting, garage door openers, sprinkler systems, or the like). For example, network device 102 may include a home automation switch that may be coupled with a home appliance. In another embodiment, a network device can allow a user to access, control, and/or configure devices, such as office-related devices (e.g., copy machine, printer, or fax machine), audio and/or video related devices (e.g., a receiver, a speaker, a projector, a DVD player, or a television), media-playback devices (e.g., a compact disc player, a CD player, or the like), computing devices (e.g., a home computer, a laptop computer, a tablet, a personal digital assistant (PDA), a computing device, or a wearable device), lighting devices (e.g., a lamp or recessed lighting), devices associated with a security system, devices associated with an alarm system, devices that can be operated in an automobile (e.g., radio devices, navigation devices), and/or the like. Data may be collected from such various sensors in raw form, or data may be processed by the sensors to create parameters or other data either developed by the sensors based on the raw data or assigned to the system by a client or other controlling device.

In another example, another type of system that may include various sensors that collect data to be processed and/or transmitted to a computing environment according to certain embodiments includes a power or energy grid. A variety of different network devices may be included in an energy grid, such as various devices within one or more power plants, energy farms (e.g., wind farm, solar farm, among others) energy storage facilities, factories, homes and businesses of consumers, among others. One or more of such devices may include one or more sensors that detect energy gain or loss, electrical input or output or loss, and a variety of other efficiencies. These sensors may collect data to inform users of how the energy grid, and individual devices within the grid, may be functioning and how they may be made more efficient.

Network device sensors may also perform processing on data it collects before transmitting the data to the computing environment 114, or before deciding whether to transmit data to the computing environment 114. For example, network devices may determine whether data collected meets certain rules, for example by comparing data or values calculated from the data and comparing that data to one or more thresholds. The network device may use this data and/or comparisons to determine if the data should be transmitted to the computing environment 214 for further use or processing.

Computing environment 214 may include machines 220 and 240. Although computing environment 214 is shown in FIG. 2 as having two machines, 220 and 240, computing environment 214 may have only one machine or may have more than two machines. The machines that make up computing environment 214 may include specialized computers, servers, or other machines that are configured to individually and/or collectively process large amounts of data. The computing environment 214 may also include storage devices that include one or more databases of structured data, such as data organized in one or more hierarchies, or unstructured data. The databases may communicate with the processing devices within computing environment 214 to distribute data to them. Since network devices may transmit data to computing environment 214, that data may be received by the computing environment 214 and subsequently stored within those storage devices. Data used by computing environment 214 may also be stored in data stores 235, which may also be a part of or connected to computing environment 214.

Computing environment 214 can communicate with various devices via one or more routers 225 or other inter-network or intra-network connection components. For example, computing environment 214 may communicate with devices 230 via one or more routers 225. Computing environment 214 may collect, analyze and/or store data from or pertaining to communications, client device operations, client rules, and/or user-associated actions stored at one or more data stores 235. Such data may influence communication routing to the devices within computing environment 214, how data is stored or processed within computing environment 214, among other actions.

Notably, various other devices can further be used to influence communication routing and/or processing between devices within computing environment 214 and with devices outside of computing environment 214. For example, as shown in FIG. 2, computing environment 214 may include a web server 240. Thus, computing environment 214 can retrieve data of interest, such as client information (e.g., product information, client rules, etc.), technical product details, news, current or predicted weather, and so on.

In addition to computing environment 214 collecting data (e.g., as received from network devices, such as sensors, and client devices or other sources) to be processed as part of a big data analytics project, it may also receive data in real time as part of a streaming analytics environment. As noted, data may be collected using a variety of sources as communicated via different kinds of networks or locally. Such data may be received on a real-time streaming basis. For example, network devices may receive data periodically from network device sensors as the sensors continuously sense, monitor and track changes in their environments. Devices within computing environment 214 may also perform pre-analysis on data it receives to determine if the data received should be processed as part of an ongoing project. The data received and collected by computing environment 214, no matter what the source or method or timing of receipt, may be processed over a period of time for a client to determine results data based on the client's needs and rules.

Figure 3:
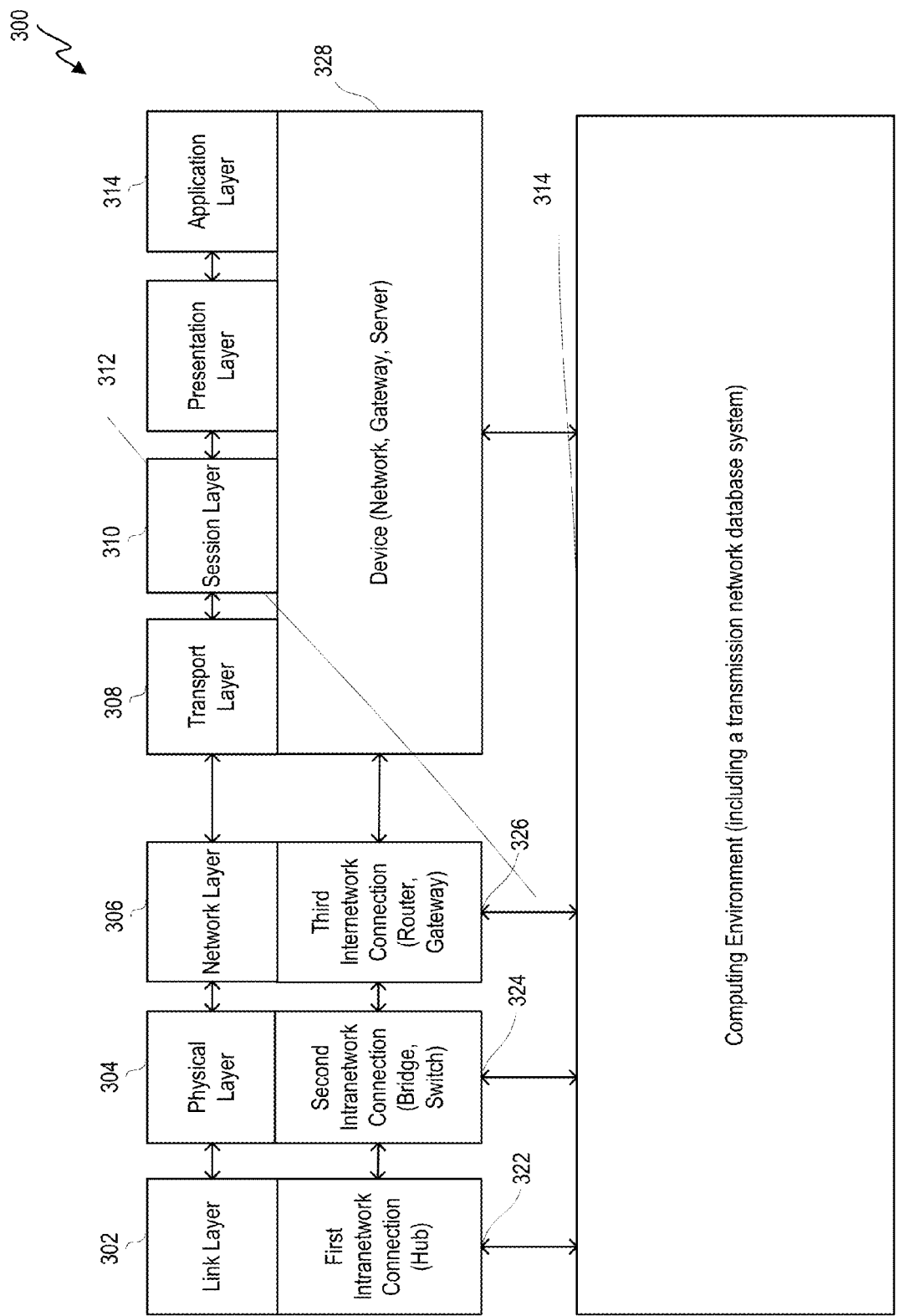
FIG. 3 illustrates a representation of a conceptual model of a communications protocol system, according to some embodiments of the present technology.

FIG. 3 illustrates a representation of a conceptual model of a communications protocol system, according to embodiments of the present technology. More specifically, FIG. 3 identifies operation of a computing environment in an Open Systems Interaction model that corresponds to various connection components. The model 300 shows, for example, how a computing environment, such as computing environment 314 (or computing environment 214 in FIG. 2) may communicate with other devices in its network, and control how communications between the computing environment and other devices are executed and under what conditions.

The model can include layers 302-314. The layers are arranged in a stack. Each layer in the stack serves the layer one level higher than it (except for the application layer, which is the highest layer), and is served by the layer one level below it (except for the physical layer, which is the lowest layer). The physical layer is the lowest layer because it receives and transmits raw bites of data, and is the farthest layer from the user in a communications system. On the other hand, the application layer is the highest layer because it interacts directly with a software application.

As noted, the model includes a physical layer 302. Physical layer 302 represents physical communication, and can define parameters of that physical communication. For example, such physical communication may come in the form of electrical, optical, or electromagnetic signals. Physical layer 302 also defines protocols that may control communications within a data transmission network.

Link layer 304 defines links and mechanisms used to transmit (i.e., move) data across a network. The link layer manages node-to-node communications, such as within a grid computing environment. Link layer 304 can detect and correct errors (e.g., transmission errors in the physical layer 302). Link layer 304 can also include a media access control (MAC) layer and logical link control (LLC) layer.

Network layer 306 defines the protocol for routing within a network. In other words, the network layer coordinates transferring data across nodes in a same network (e.g., such as a grid computing environment). Network layer 306 can also define the processes used to structure local addressing within the network.

Transport layer 308 can manage the transmission of data and the quality of the transmission and/or receipt of that data. Transport layer 308 can provide a protocol for transferring data, such as, for example, a Transmission Control Protocol (TCP). Transport layer 308 can assemble and disassemble data frames for transmission. The transport layer can also detect transmission errors occurring in the layers below it.

Session layer 310 can establish, maintain, and manage communication connections between devices on a network. In other words, the session layer controls the dialogues or nature of communications between network devices on the network. The session layer may also establish checkpointing, adjournment, termination, and restart procedures.

Presentation layer 312 can provide translation for communications between the application and network layers. In other words, this layer may encrypt, decrypt and/or format data based on data types known to be accepted by an application or network layer.

Application layer 314 interacts directly with software applications and end users, and manages communications between them. Application layer 314 can identify destinations, local resource states or availability and/or communication content or formatting using the applications.

Intra-network connection components 322 and 324 are shown to operate in lower levels, such as physical layer 302 and link layer 304, respectively. For example, a hub can operate in the physical layer, a switch can operate in the physical layer, and a router can operate in the network layer. Inter-network connection components 326 and 328 are shown to operate on higher levels, such as layers 306-314. For example, routers can operate in the network layer and network devices can operate in the transport, session, presentation, and application layers.

As noted, a computing environment 314 can interact with and/or operate on, in various embodiments, one, more, all or any of the various layers. For example, computing environment 314 can interact with a hub (e.g., via the link layer) so as to adjust which devices the hub communicates with. The physical layer may be served by the link layer, so it may implement such data from the link layer. For example, the computing environment 314 may control which devices it will receive data from. For example, if the computing environment 314 knows that a certain network device has turned off, broken, or otherwise become unavailable or unreliable, the computing environment 314 may instruct the hub to prevent any data from being transmitted to the computing environment 314 from that network device. Such a process may be beneficial to avoid receiving data that is inaccurate or that has been influenced by an uncontrolled environment. As another example, computing environment 314 can communicate with a bridge, switch, router or gateway and influence which device within the system (e.g., system 200) the component selects as a destination. In some embodiments, computing environment 314 can interact with various layers by exchanging communications with equipment operating on a particular layer by routing or modifying existing communications. In another embodiment, such as in a grid computing environment, a node may determine how data within the environment should be routed (e.g., which node should receive certain data) based on certain parameters or information provided by other layers within the model.

As noted, the computing environment 314 may be a part of a communications grid environment, the communications of which may be implemented as shown in the protocol of FIG. 3. For example, referring back to FIG. 2, one or more of machines 220 and 240 may be part of a communications grid computing environment. A gridded computing environment may be employed in a distributed system with non-interactive workloads where data resides in memory on the machines, or compute nodes. In such an environment, analytic code, instead of a database management system, controls the processing performed by the nodes. Data is co-located by pre-distributing it to the grid nodes, and the analytic code on each node loads the local data into memory. Each node may be assigned a particular task such as a portion of a processing project, or to organize or control other nodes within the grid.

Figure 4:
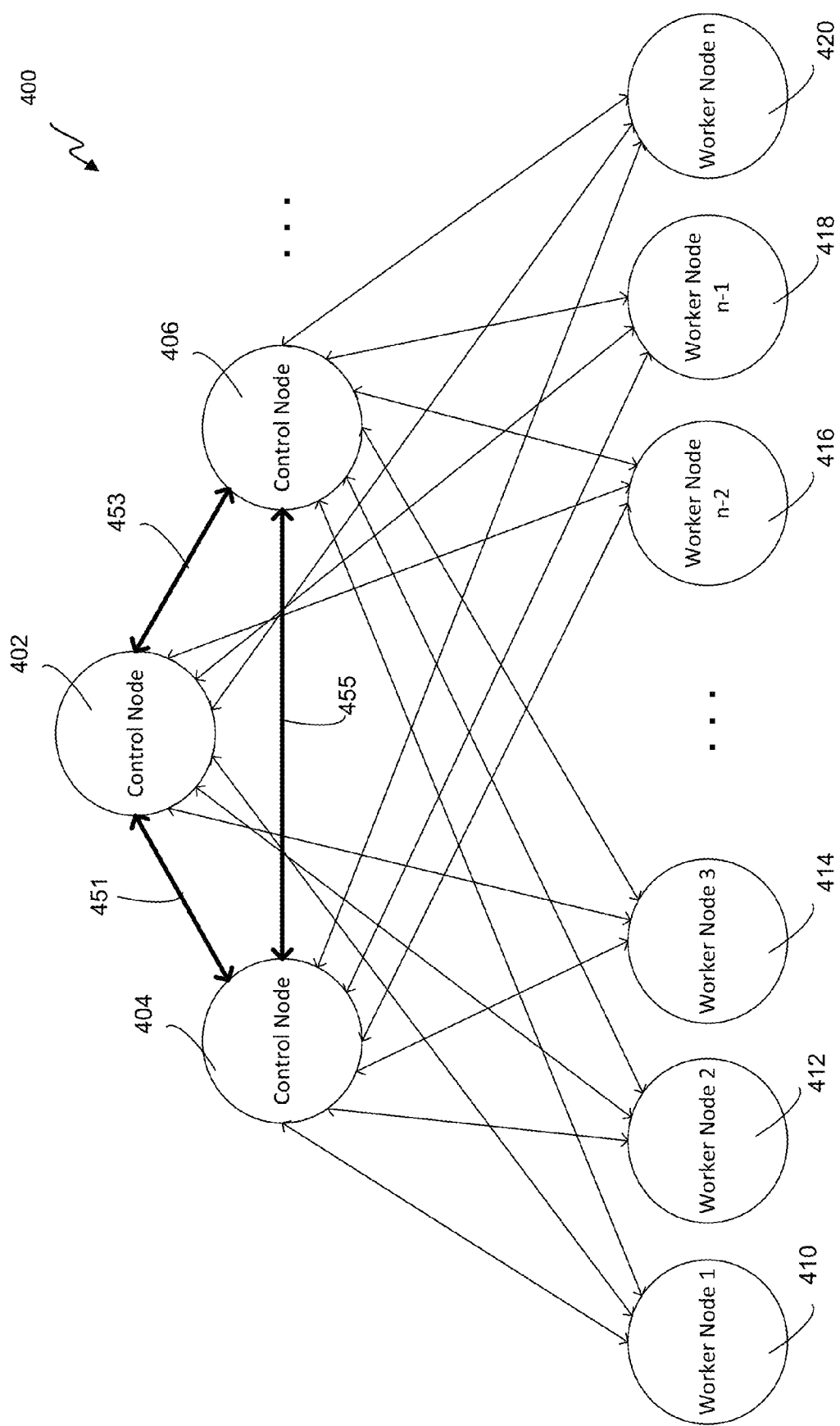
FIG. 4 illustrates a communications grid computing system including a variety of control and worker nodes, according to some embodiments of the present technology.

FIG. 4 illustrates a communications grid computing system 400 including a variety of control and worker nodes, according to embodiments of the present technology. Communications grid computing system 400 includes three control nodes and one or more worker nodes. Communications grid computing system 400 includes control nodes 402, 404, and 406. The control nodes are communicatively connected via communication paths 451, 453, and 455. Therefore, the control nodes may transmit information (e.g., related to the communications grid or notifications), to and receive information from each other. Although communications grid computing system 400 is shown in FIG. 4 as including three control nodes, the communications grid may include more or less than three control nodes.

Communications grid computing system (or just "communications grid") 400 also includes one or more worker nodes. Shown in FIG. 4 are six worker nodes 410-420. Although FIG. 4 shows six worker nodes, a communications grid according to embodiments of the present technology may include more or less than six worker nodes. The number of worker nodes included in a communications grid may be dependent upon how large the project or data set is being processed by the communications grid, the capacity of each worker node, the time designated for the communications grid to complete the project, among others. Each worker node within the communications grid 400 may be connected (wired or wirelessly, and directly or indirectly) to control nodes 402-406. Therefore, each worker node may receive information from the control nodes (e.g., an instruction to perform work on a project) and may transmit information to the control nodes (e.g., a result from work performed on a project). Furthermore, worker nodes may communicate with each other (either directly or indirectly). For example, worker nodes may transmit data between each other related to a job being performed or an individual task within a job being performed by that worker node. However, in certain embodiments, worker nodes may not, for example, be connected (communicatively or otherwise) to certain other worker nodes. In an embodiment, worker nodes may only be able to communicate with the control node that controls it, and may not be able to communicate with other worker nodes in the communications grid, whether they are other worker nodes controlled by the control node that controls the worker node, or worker nodes that are controlled by other control nodes in the communications grid.

A control node may connect with an external device with which the control node may communicate (e.g., a grid user, such as a server or computer, may connect to a controller of the grid). For example, a server or computer may connect to control nodes and may transmit a project or job to the node. The project may include a data set. The data set may be of any size. Once the control node receives such a project including a large data set, the control node may distribute the data set or projects related to the data set to be performed by worker nodes. Alternatively, for a project including a large data set, the data set may be receive or stored by a machine other than a control node (e.g., a Hadoop data node).

Control nodes may maintain knowledge of the status of the nodes in the grid (i.e., grid status information), accept work requests from clients, subdivide the work across worker nodes, coordinate the worker nodes, among other responsibilities. Worker nodes may accept work requests from a control node and provide the control node with results of the work performed by the worker node. A grid may be started from a single node (e.g., a machine, computer, server, etc.). This first node may be assigned or may start as the primary control node that will control any additional nodes that enter the grid.

When a project is submitted for execution (e.g., by a client or a controller of the grid) it may be assigned to a set of nodes. After the nodes are assigned to a project, a data structure (i.e., a communicator) may be created. The communicator may be used by the project for information to be shared between the project code running on each node. A communication handle may be created on each node. A handle, for example, is a reference to the communicator that is valid within a single process on a single node, and the handle may be used when requesting communications between nodes.

A control node, such as control node 402, may be designated as the primary control node. A server, computer or other external device may connect to the primary control node. Once the control node receives a project, the primary control node may distribute portions of the project to its worker nodes for execution. For example, when a project is initiated on communications grid 400, primary control node 402 controls the work to be performed for the project in order to complete the project as requested or instructed. The primary control node may distribute work to the worker nodes based on various factors, such as which subsets or portions of projects may be completed most efficiently and in the correct amount of time. For example, a worker node may perform analysis on a portion of data that is already local (e.g., stored on) the worker node. The primary control node also coordinates and processes the results of the work performed by each worker node after each worker node executes and completes its job. For example, the primary control node may receive a result from one or more worker nodes, and the control node may organize (e.g., collect and assemble) the results received and compile them to produce a complete result for the project received from the end user.

Any remaining control nodes, such as control nodes 404 and 406, may be assigned as backup control nodes for the project. In an embodiment, backup control nodes may not control any portion of the project. Instead, backup control nodes may serve as a backup for the primary control node and take over as primary control node if the primary control node were to fail. If a communications grid were to include only a single control node, and the control node were to fail (e.g., the control node is shut off or breaks) then the communications grid as a whole may fail and any project or job being run on the communications grid may fail and may not complete. While the project may be run again, such a failure may cause a delay (severe delay in some cases, such as overnight delay) in completion of the project. Therefore, a grid with multiple control nodes, including a backup control node, may be beneficial.

To add another node or machine to the grid, the primary control node may open a pair of listening sockets, for example. A socket may be used to accept work requests from clients, and the second socket may be used to accept connections from other grid nodes). The primary control node may be provided with a list of other nodes (e.g., other machines, computers, servers) that will participate in the grid, and the role that each node will fill in the grid. Upon startup of the primary control node (e.g., the first node on the grid), the primary control node may use a network protocol to start the server process on every other node in the grid. Command line parameters, for example, may inform each node of one or more pieces of information, such as: the role that the node will have in the grid, the host name of the primary control node, the port number on which the primary control node is accepting connections from peer nodes, among others. The information may also be provided in a configuration file, transmitted over a secure shell tunnel, recovered from a configuration server, among others. While the other machines in the grid may not initially know about the configuration of the grid, that information may also be sent to each other node by the primary control node. Updates of the grid information may also be subsequently sent to those nodes.

For any control node other than the primary control node added to the grid, the control node may open three sockets. The first socket may accept work requests from clients, the second socket may accept connections from other grid members, and the third socket may connect (e.g., permanently) to the primary control node. When a control node (e.g., primary control node) receives a connection from another control node, it first checks to see if the peer node is in the list of configured nodes in the grid. If it is not on the list, the control node may clear the connection. If it is on the list, it may then attempt to authenticate the connection. If authentication is successful, the authenticating node may transmit information to its peer, such as the port number on which a node is listening for connections, the host name of the node, information about how to authenticate the node, among other information. When a node, such as the new control node, receives information about another active node, it will check to see if it already has a connection to that other node. If it does not have a connection to that node, it may then establish a connection to that control node.

Any worker node added to the grid may establish a connection to the primary control node and any other control nodes on the grid. After establishing the connection, it may authenticate itself to the grid (e.g., any control nodes, including both primary and backup, or a server or user controlling the grid). After successful authentication, the worker node may accept configuration information from the control node.

When a node joins a communications grid (e.g., when the node is powered on or connected to an existing node on the grid or both), the node is assigned (e.g., by an operating system of the grid) a universally unique identifier (UUID). This unique identifier may help other nodes and external entities (devices, users, etc.) to identify the node and distinguish it from other nodes. When a node is connected to the grid, the node may share its unique identifier with the other nodes in the grid. Since each node may share its unique identifier, each node may know the unique identifier of every other node on the grid. Unique identifiers may also designate a hierarchy of each of the nodes (e.g., backup control nodes) within the grid. For example, the unique identifiers of each of the backup control nodes may be stored in a list of backup control nodes to indicate an order in which the backup control nodes will take over for a failed primary control node to become a new primary control node. However, a hierarchy of nodes may also be determined using methods other than using the unique identifiers of the nodes. For example, the hierarchy may be predetermined, or may be assigned based on other predetermined factors.

The grid may add new machines at any time (e.g., initiated from any control node). Upon adding a new node to the grid, the control node may first add the new node to its table of grid nodes. The control node may also then notify every other control node about the new node. The nodes receiving the notification may acknowledge that they have updated their configuration information.

Primary control node 402 may, for example, transmit one or more communications to backup control nodes 404 and 406 (and, for example, to other control or worker nodes within the communications grid). Such communications may sent periodically, at fixed time intervals, between known fixed stages of the project's execution, among other protocols. The communications transmitted by primary control node 402 may be of varied types and may include a variety of types of information. For example, primary control node 402 may transmit snapshots (e.g., status information) of the communications grid so that backup control node 404 always has a recent snapshot of the communications grid. The snapshot or grid status may include, for example, the structure of the grid (including, for example, the worker nodes in the grid, unique identifiers of the nodes, or their relationships with the primary control node) and the status of a project (including, for example, the status of each worker node's portion of the project). The snapshot may also include analysis or results received from worker nodes in the communications grid. The backup control nodes may receive and store the backup data received from the primary control node. The backup control nodes may transmit a request for such a snapshot (or other information) from the primary control node, or the primary control node may send such information periodically to the backup control nodes.

As noted, the backup data may allow the backup control node to take over as primary control node if the primary control node fails without requiring the grid to start the project over from scratch. If the primary control node fails, the backup control node that will take over as primary control node may retrieve the most recent version of the snapshot received from the primary control node and use the snapshot to continue the project from the stage of the project indicated by the backup data. This may prevent failure of the project as a whole.

A backup control node may use various methods to determine that the primary control node has failed. In one example of such a method, the primary control node may transmit (e.g., periodically) a communication to the backup control node that indicates that the primary control node is working and has not failed, such as a heartbeat communication. The backup control node may determine that the primary control node has failed if the backup control node has not received a heartbeat communication for a certain predetermined period of time. Alternatively, a backup control node may also receive a communication from the primary control node itself (before it failed) or from a worker node that the primary control node has failed, for example because the primary control node has failed to communicate with the worker node.

Different methods may be performed to determine which backup control node of a set of backup control nodes (e.g., backup control nodes 404 and 406) will take over for failed primary control node 402 and become the new primary control node. For example, the new primary control node may be chosen based on a ranking or "hierarchy" of backup control nodes based on their unique identifiers. In an alternative embodiment, a backup control node may be assigned to be the new primary control node by another device in the communications grid or from an external device (e.g., a system infrastructure or an end user, such as a server or computer, controlling the communications grid). In another alternative embodiment, the backup control node that takes over as the new primary control node may be designated based on bandwidth or other statistics about the communications grid.

A worker node within the communications grid may also fail. If a worker node fails, work being performed by the failed worker node may be redistributed amongst the operational worker nodes. In an alternative embodiment, the primary control node may transmit a communication to each of the operable worker nodes still on the communications grid that each of the worker nodes should purposefully fail also. After each of the worker nodes fail, they may each retrieve their most recent saved checkpoint of their status and re-start the project from that checkpoint to minimize lost progress on the project being executed.

Figure 5:
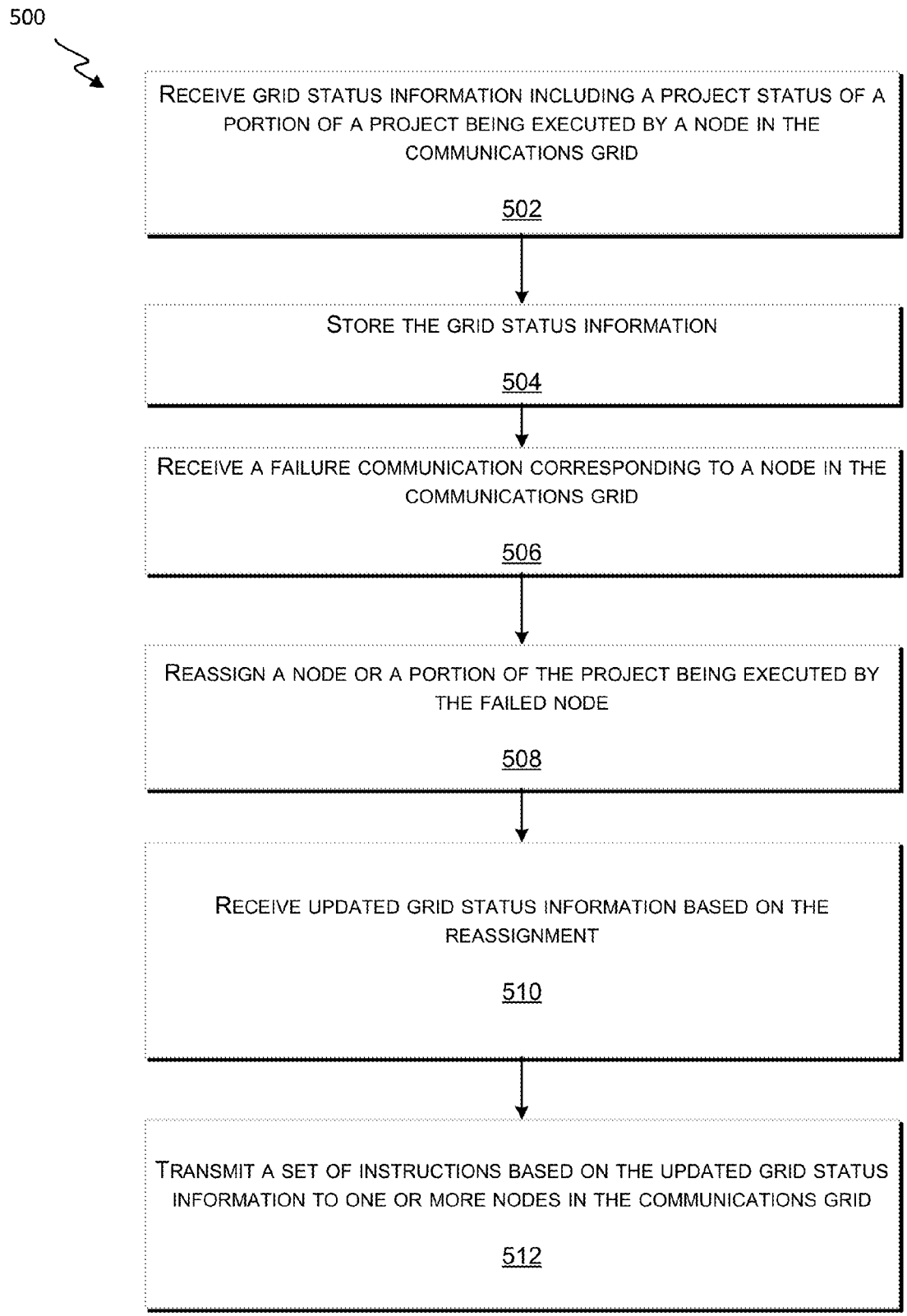
FIG. 5 illustrates a flow chart showing an example process for adjusting a communications grid or a work project in a communications grid after a failure of a node, according to some embodiments of the present technology.

FIG. 5 illustrates a flow chart showing an example process for adjusting a communications grid or a work project in a communications grid after a failure of a node, according to embodiments of the present technology. The process may include, for example, receiving grid status information including a project status of a portion of a project being executed by a node in the communications grid, as described in operation 502. For example, a control node (e.g., a backup control node connected to a primary control node and a worker node on a communications grid) may receive grid status information, where the grid status information includes a project status of the primary control node or a project status of the worker node. The project status of the primary control node and the project status of the worker node may include a status of one or more portions of a project being executed by the primary and worker nodes in the communications grid. The process may also include storing the grid status information, as described in operation 504. For example, a control node (e.g., a backup control node) may store the received grid status information locally within the control node. Alternatively, the grid status information may be sent to another device for storage where the control node may have access to the information.

The process may also include receiving a failure communication corresponding to a node in the communications grid in operation 506. For example, a node may receive a failure communication including an indication that the primary control node has failed, prompting a backup control node to take over for the primary control node. In an alternative embodiment, a node may receive a failure that a worker node has failed, prompting a control node to reassign the work being performed by the worker node. The process may also include reassigning a node or a portion of the project being executed by the failed node, as described in operation 508. For example, a control node may designate the backup control node as a new primary control node based on the failure communication upon receiving the failure communication. If the failed node is a worker node, a control node may identify a project status of the failed worker node using the snapshot of the communications grid, where the project status of the failed worker node includes a status of a portion of the project being executed by the failed worker node at the failure time.

The process may also include receiving updated grid status information based on the reassignment, as described in operation 510, and transmitting a set of instructions based on the updated grid status information to one or more nodes in the communications grid, as described in operation 512. The updated grid status information may include an updated project status of the primary control node or an updated project status of the worker node. The updated information may be transmitted to the other nodes in the grid to update their stale stored information.

Figure 6:
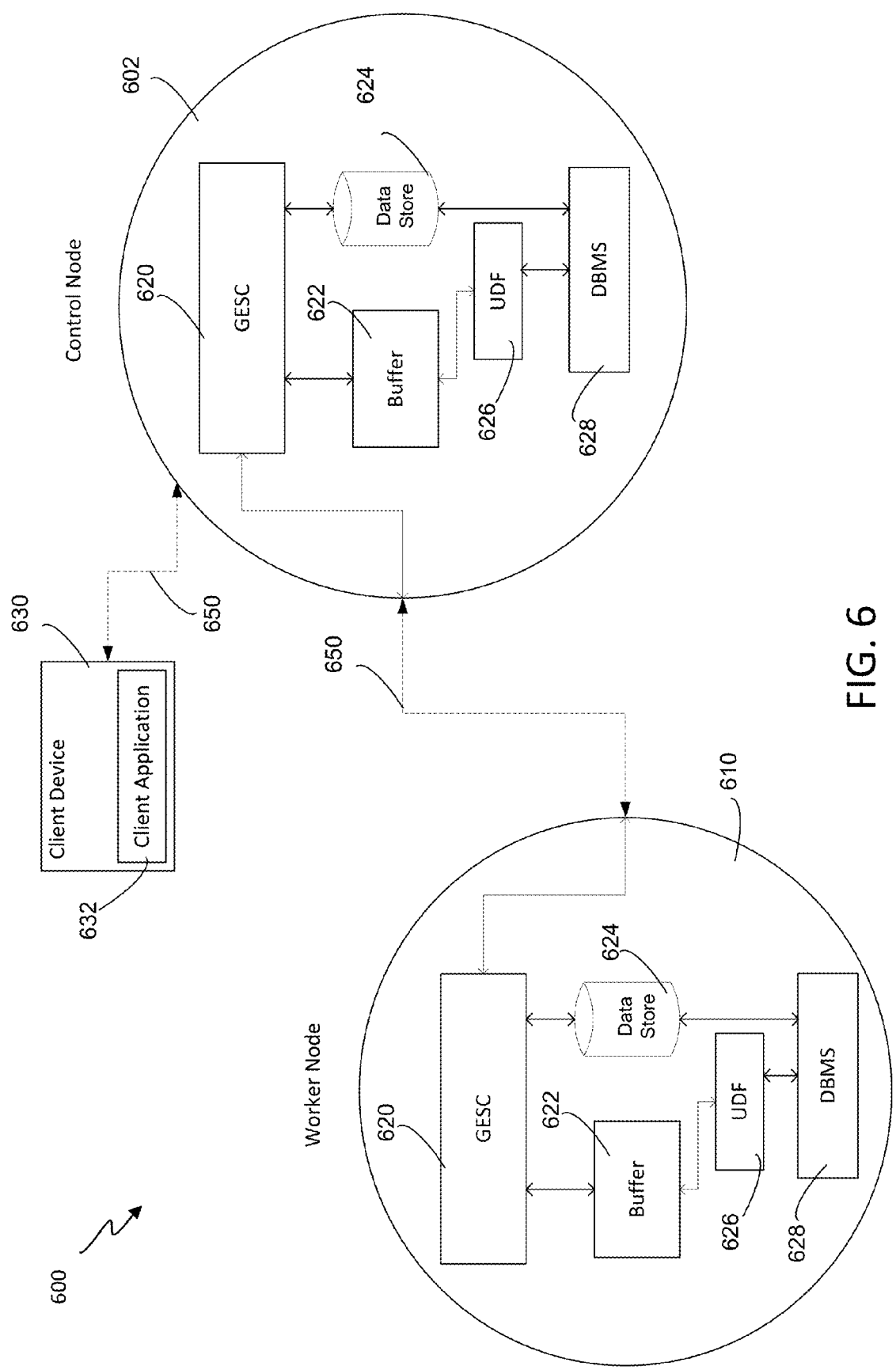
FIG. 6 illustrates a portion of a communications grid computing system including a control node and a worker node, according to some embodiments of the present technology.

FIG. 6 illustrates a portion of a communications grid computing system 600 including a control node and a worker node, according to embodiments of the present technology. Communications grid 600 computing system includes one control node (control node 602) and one worker node (worker node 610) for purposes of illustration, but may include more worker and/or control nodes. The control node 602 is communicatively connected to worker node 610 via communication path 650. Therefore, control node 602 may transmit information (e.g., related to the communications grid or notifications), to and receive information from worker node 610 via path 650.

Similar to in FIG. 4, communications grid computing system (or just "communications grid") 600 includes data processing nodes (control node 602 and worker node 610). Nodes 602 and 610 comprise multi-core data processors. Each node 602 and 610 includes a grid-enabled software component (GESC) 620 that executes on the data processor associated with that node and interfaces with buffer memory 622 also associated with that node. Each node 602 and 610 includes a database management software (DBMS) 628 that executes on a database server (not shown) at control node 602 and on a database server (not shown) at worker node 610.

Each node also includes a data store 624. Data stores 624, similar to network-attached data stores 110 in FIG. 1 and data stores 235 in FIG. 2, are used to store data to be processed by the nodes in the computing environment. Data stores 624 may also store any intermediate or final data generated by the computing system after being processed, for example in non-volatile memory. However in certain embodiments, the configuration of the grid computing environment allows its operations to be performed such that intermediate and final data results can be stored solely in volatile memory (e.g., RAM), without a requirement that intermediate or final data results be stored to non-volatile types of memory. Storing such data in volatile memory may be useful in certain situations, such as when the grid receives queries (e.g., ad hoc) from a client and when responses, which are generated by processing large amounts of data, need to be generated quickly or on-the-fly. In such a situation, the grid may be configured to retain the data within memory so that responses can be generated at different levels of detail and so that a client may interactively query against this information.

Each node also includes a user-defined function (UDF) 626. The UDF provides a mechanism for the DMBS 628 to transfer data to or receive data from the database stored in the data stores 624 that are managed by the DBMS. For example, UDF 626 can be invoked by the DBMS to provide data to the GESC for processing. The UDF 626 may establish a socket connection (not shown) with the GESC to transfer the data. Alternatively, the UDF 626 can transfer data to the GESC by writing data to shared memory accessible by both the UDF and the GESC.

The GESC 620 at the nodes 602 and 620 may be connected via a network, such as network 108 shown in FIG. 1. Therefore, nodes 602 and 620 can communicate with each other via the network using a predetermined communication protocol such as, for example, the Message Passing Interface (MPI). Each GESC 620 can engage in point-to-point communication with the GESC at another node or in collective communication with multiple GESCs via the network. The GESC 620 at each node may contain identical (or nearly identical) software instructions. Each node may be capable of operating as either a control node or a worker node. The GESC at the control node 602 can communicate, over a communication path 652, with a client device 630. More specifically, control node 602 may communicate with client application 632 hosted by the client device 630 to receive queries and to respond to those queries after processing large amounts of data.

DMBS 628 may control the creation, maintenance, and use of database or data structure (not shown) within a nodes 602 or 610. The database may organize data stored in data stores 624. The DMBS 628 at control node 602 may accept requests for data and transfer the appropriate data for the request. With such a process, collections of data may be distributed across multiple physical locations. In this example, each node 602 and 610 stores a portion of the total data managed by the management system in its associated data store 624.

Furthermore, the DBMS may be responsible for protecting against data loss using replication techniques. Replication includes providing a backup copy of data stored on one node on one or more other nodes. Therefore, if one node fails, the data from the failed node can be recovered from a replicated copy residing at another node. However, as described herein with respect to FIG. 4, data or status information for each node in the communications grid may also be shared with each node on the grid.

Figure 7:
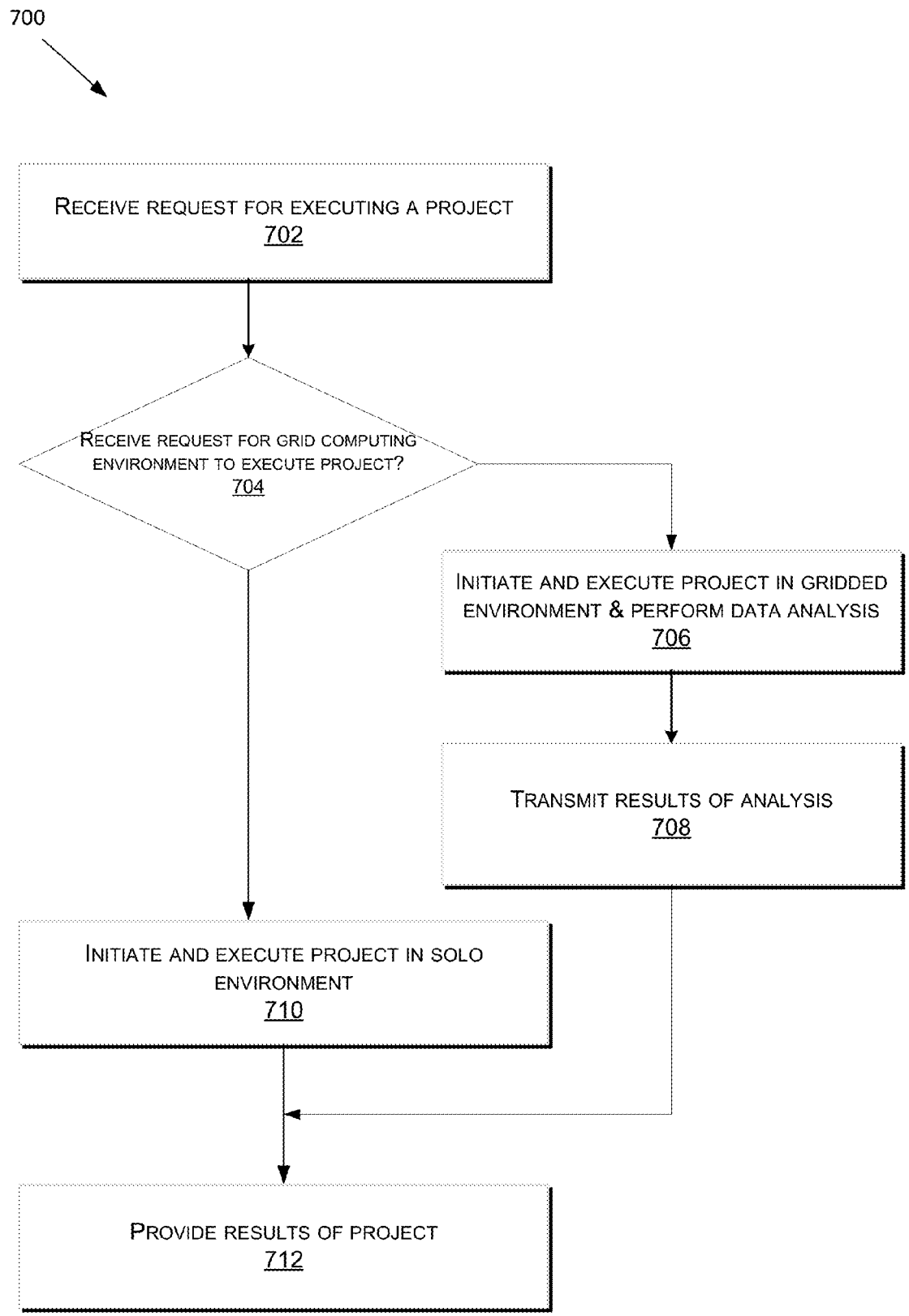
FIG. 7 illustrates a flow chart showing an example process for executing a data analysis or processing project, according to some embodiments of the present technology.

FIG. 7 illustrates a flow chart showing an example method for executing a project within a grid computing system, according to embodiments of the present technology. As described with respect to FIG. 6, the GESC at the control node may transmit data with a client device (e.g., client device 630) to receive queries for executing a project and to respond to those queries after large amounts of data have been processed. The query may be transmitted to the control node, where the query may include a request for executing a project, as described in operation 702. The query can contain instructions on the type of data analysis to be performed in the project and whether the project should be executed using the grid-based computing environment, as shown in operation 704.

To initiate the project, the control node may determine if the query requests use of the grid-based computing environment to execute the project. If the determination is no, then the control node initiates execution of the project in a solo environment (e.g., at the control node), as described in operation 710. If the determination is yes, the control node may initiate execution of the project in the grid-based computing environment, as described in operation 706. In such a situation, the request may include a requested configuration of the grid. For example, the request may include a number of control nodes and a number of worker nodes to be used in the grid when executing the project. After the project has been completed, the control node may transmit results of the analysis yielded by the grid, as described in operation 708. Whether the project is executed in a solo or grid-based environment, the control node provides the results of the project.

As noted with respect to FIG. 2, the computing environments described herein may collect data (e.g., as received from network devices, such as sensors, such as network devices 204-209 in FIG. 2, and client devices or other sources) to be processed as part of a data analytics project, and data may be received in real time as part of a streaming analytics environment (e.g., ESP). Data may be collected using a variety of sources as communicated via different kinds of networks or locally, such as on a real-time streaming basis. For example, network devices may receive data periodically from network device sensors as the sensors continuously sense, monitor and track changes in their environments. More specifically, an increasing number of distributed applications develop or produce continuously flowing data from distributed sources by applying queries to the data before distributing the data to geographically distributed recipients. An event stream processing engine (ESPE) may continuously apply the queries to the data as it is received and determines which entities should receive the data. Client or other devices may also subscribe to the ESPE or other devices processing ESP data so that they can receive data after processing, based on for example the entities determined by the processing engine. For example, client devices 230 in FIG. 2 may subscribe to the ESPE in computing environment 214. In another example, event subscription devices 874a-c, described further with respect to FIG. 10, may also subscribe to the ESPE. The ESPE may determine or define how input data or event streams from network devices or other publishers (e.g., network devices 204-209 in FIG. 2) are transformed into meaningful output data to be consumed by subscribers, such as for example client devices 230 in FIG. 2.

FIG. 8 illustrates a block diagram including components of an Event Stream Processing Engine (ESPE), according to embodiments of the present technology. ESPE 800 may include one or more projects 802. A project may be described as a second-level container in an engine model managed by ESPE 800 where a thread pool size for the project may be defined by a user. Each project of the one or more projects 802 may include one or more continuous queries 804 that contain data flows, which are data transformations of incoming event streams. The one or more continuous queries 804 may include one or more source windows 806 and one or more derived windows 808.

The ESPE may receive streaming data over a period of time related to certain events, such as events or other data sensed by one or more network devices. The ESPE may perform operations associated with processing data created by the one or more devices. For example, the ESPE may receive data from the one or more network devices 204-209 shown in FIG. 2. As noted, the network devices may include sensors that sense different aspects of their environments, and may collect data over time based on those sensed observations. For example, the ESPE may be implemented within one or more of machines 220 and 240 shown in FIG. 2. The ESPE may be implemented within such a machine by an ESP application. An ESP application may embed an ESPE with its own dedicated thread pool or pools into its application space where the main application thread can do application-specific work and the ESPE processes event streams at least by creating an instance of a model into processing objects.

The engine container is the top-level container in a model that manages the resources of the one or more projects 802. In an illustrative embodiment, for example, there may be only one ESPE 800 for each instance of the ESP application, and ESPE 800 may have a unique engine name. Additionally, the one or more projects 802 may each have unique project names, and each query may have a unique continuous query name and begin with a uniquely named source window of the one or more source windows 806. ESPE 800 may or may not be persistent.

Continuous query modeling involves defining directed graphs of windows for event stream manipulation and transformation. A window in the context of event stream manipulation and transformation is a processing node in an event stream processing model. A window in a continuous query can perform aggregations, computations, pattern-matching, and other operations on data flowing through the window. A continuous query may be described as a directed graph of source, relational, pattern matching, and procedural windows. The one or more source windows 806 and the one or more derived windows 808 represent continuously executing queries that generate updates to a query result set as new event blocks stream through ESPE 800. A directed graph, for example, is a set of nodes connected by edges, where the edges have a direction associated with them.

An event object may be described as a packet of data accessible as a collection of fields, with at least one of the fields defined as a key or unique identifier (ID). The event object may be created using a variety of formats including binary, alphanumeric, XML, etc. Each event object may include one or more fields designated as a primary identifier (ID) for the event so ESPE 800 can support operation codes (opcodes) for events including insert, update, upsert, and delete. Upsert opcodes update the event if the key field already exists; otherwise, the event is inserted. For illustration, an event object may be a packed binary representation of a set of field values and include both metadata and field data associated with an event. The metadata may include an opcode indicating if the event represents an insert, update, delete, or upsert, a set of flags indicating if the event is a normal, partial-update, or a retention generated event from retention policy management, and a set of microsecond timestamps that can be used for latency measurements.

An event block object may be described as a grouping or package of event objects. An event stream may be described as a flow of event block objects. A continuous query of the one or more continuous queries 804 transforms a source event stream made up of streaming event block objects published into ESPE 800 into one or more output event streams using the one or more source windows 806 and the one or more derived windows 808. A continuous query can also be thought of as data flow modeling.

The one or more source windows 806 are at the top of the directed graph and have no windows feeding into them. Event streams are published into the one or more source windows 806, and from there, the event streams may be directed to the next set of connected windows as defined by the directed graph. The one or more derived windows 808 are all instantiated windows that are not source windows and that have other windows streaming events into them. The one or more derived windows 808 may perform computations or transformations on the incoming event streams. The one or more derived windows 808 transform event streams based on the window type (that is operators such as join, filter, compute, aggregate, copy, pattern match, procedural, union, etc.) and window settings. As event streams are published into ESPE 800, they are continuously queried, and the resulting sets of derived windows in these queries are continuously updated.

FIG. 9 illustrates a flow chart showing an example process including operations performed by an event stream processing engine, according to some embodiments of the present technology. As noted, the ESPE 800 (or an associated ESP application) defines how input event streams are transformed into meaningful output event streams. More specifically, the ESP application may define how input event streams from publishers (e.g., network devices providing sensed data) are transformed into meaningful output event streams consumed by subscribers (e.g., a data analytics project being executed by a machine or set of machines).

Within the application, a user may interact with one or more user interface windows presented to the user in a display under control of the ESPE independently or through a browser application in an order selectable by the user. For example, a user may execute an ESP application, which causes presentation of a first user interface window, which may include a plurality of menus and selectors such as drop down menus, buttons, text boxes, hyperlinks, etc. associated with the ESP application as understood by a person of skill in the art. As further understood by a person of skill in the art, various operations may be performed in parallel, for example, using a plurality of threads.

At operation 900, an ESP application may define and start an ESPE, thereby instantiating an ESPE at a device, such as machine 220 and/or 240. In an operation 902, the engine container is created. For illustration, ESPE 800 may be instantiated using a function call that specifies the engine container as a manager for the model.

In an operation 904, the one or more continuous queries 804 are instantiated by ESPE 800 as a model. The one or more continuous queries 804 may be instantiated with a dedicated thread pool or pools that generate updates as new events stream through ESPE 800. For illustration, the one or more continuous queries 804 may be created to model business processing logic within ESPE 800, to predict events within ESPE 800, to model a physical system within ESPE 800, to predict the physical system state within ESPE 800, etc. For example, as noted, ESPE 800 may be used to support sensor data monitoring and management (e.g., sensing may include force, torque, load, strain, position, temperature, air pressure, fluid flow, chemical properties, resistance, electromagnetic fields, radiation, irradiance, proximity, acoustics, moisture, distance, speed, vibrations, acceleration, electrical potential, or electrical current, etc.).

ESPE 800 may analyze and process events in motion or "event streams." Instead of storing data and running queries against the stored data, ESPE 800 may store queries and stream data through them to allow continuous analysis of data as it is received. The one or more source windows 806 and the one or more derived windows 808 may be created based on the relational, pattern matching, and procedural algorithms that transform the input event streams into the output event streams to model, simulate, score, test, predict, etc. based on the continuous query model defined and application to the streamed data.

In an operation 906, a publish/subscribe (pub/sub) capability is initialized for ESPE 800. In an illustrative embodiment, a pub/sub capability is initialized for each project of the one or more projects 802. To initialize and enable pub/sub capability for ESPE 800, a port number may be provided. Pub/sub clients can use a host name of an ESP device running the ESPE and the port number to establish pub/sub connections to ESPE 800.

FIG. 10 illustrates an ESP system 850 interfacing between publishing device 872 and event subscribing devices 874a-c, according to embodiments of the present technology. ESP system 850 may include ESP device or subsystem 851, event publishing device 872, an event subscribing device A 874a, an event subscribing device B 874b, and an event subscribing device C 874c. Input event streams are output to ESP device 851 by publishing device 872. In alternative embodiments, the input event streams may be created by a plurality of publishing devices. The plurality of publishing devices further may publish event streams to other ESP devices. The one or more continuous queries instantiated by ESPE 800 may analyze and process the input event streams to form output event streams output to event subscribing device A 874a, event subscribing device B 874b, and event subscribing device C 874c. ESP system 850 may include a greater or a fewer number of event subscribing devices of event subscribing devices.

Publish-subscribe is a message-oriented interaction paradigm based on indirect addressing. Processed data recipients specify their interest in receiving information from ESPE 800 by subscribing to specific classes of events, while information sources publish events to ESPE 800 without directly addressing the receiving parties. ESPE 800 coordinates the interactions and processes the data. In some cases, the data source receives confirmation that the published information has been received by a data recipient.

A publish/subscribe API may be described as a library that enables an event publisher, such as publishing device 872, to publish event streams into ESPE 800 or an event subscriber, such as event subscribing device A 874a, event subscribing device B 874b, and event subscribing device C 874c, to subscribe to event streams from ESPE 800. For illustration, one or more publish/subscribe APIs may be defined. Using the publish/subscribe API, an event publishing application may publish event streams into a running event stream processor project source window of ESPE 800, and the event subscription application may subscribe to an event stream processor project source window of ESPE 800.

The publish/subscribe API provides cross-platform connectivity and endianness compatibility between ESP application and other networked applications, such as event publishing applications instantiated at publishing device 872, and event subscription applications instantiated at one or more of event subscribing device A 874a, event subscribing device B 874b, and event subscribing device C 874c.

Referring back to FIG. 9, operation 906 initializes the publish/subscribe capability of ESPE 800. In an operation 908, the one or more projects 802 are started. The one or more started projects may run in the background on an ESP device. In an operation 910, an event block object is received from one or more computing device of the event publishing device 872.

ESP subsystem 800 may include a publishing client 852, ESPE 800, a subscribing client A 854, a subscribing client B 856, and a subscribing client C 858. Publishing client 852 may be started by an event publishing application executing at publishing device 872 using the publish/subscribe API. Subscribing client A 854 may be started by an event subscription application A, executing at event subscribing device A 874a using the publish/subscribe API. Subscribing client B 856 may be started by an event subscription application B executing at event subscribing device B 874b using the publish/subscribe API. Subscribing client C 858 may be started by an event subscription application C executing at event subscribing device C 874c using the publish/subscribe API.

An event block object containing one or more event objects is injected into a source window of the one or more source windows 806 from an instance of an event publishing application on event publishing device 872. The event block object may generated, for example, by the event publishing application and may be received by publishing client 852. A unique ID may be maintained as the event block object is passed between the one or more source windows 806 and/or the one or more derived windows 808 of ESPE 800, and to subscribing client A 854, subscribing client B 806, and subscribing client C 808 and to event subscription device A 874a, event subscription device B 874b, and event subscription device C 874c. Publishing client 852 may further generate and include a unique embedded transaction ID in the event block object as the event block object is processed by a continuous query, as well as the unique ID that publishing device 872 assigned to the event block object.

In an operation 912, the event block object is processed through the one or more continuous queries 804. In an operation 914, the processed event block object is output to one or more computing devices of the event subscribing devices 874a-c. For example, subscribing client A 804, subscribing client B 806, and subscribing client C 808 may send the received event block object to event subscription device A 874a, event subscription device B 874b, and event subscription device C 874c, respectively.

ESPE 800 maintains the event block containership aspect of the received event blocks from when the event block is published into a source window and works its way through the directed graph defined by the one or more continuous queries 804 with the various event translations before being output to subscribers. Subscribers can correlate a group of subscribed events back to a group of published events by comparing the unique ID of the event block object that a publisher, such as publishing device 872, attached to the event block object with the event block ID received by the subscriber.

In an operation 916, a determination is made concerning whether or not processing is stopped. If processing is not stopped, processing continues in operation 910 to continue receiving the one or more event streams containing event block objects from the, for example, one or more network devices. If processing is stopped, processing continues in an operation 918. In operation 918, the started projects are stopped. In operation 920, the ESPE is shutdown.

As noted, in some embodiments, big data is processed for an analytics project after the data is received and stored. In other embodiments, distributed applications process continuously flowing data in real-time from distributed sources by applying queries to the data before distributing the data to geographically distributed recipients. As noted, an event stream processing engine (ESPE) may continuously apply the queries to the data as it is received and determines which entities receive the processed data. This allows for large amounts of data being received and/or collected in a variety of environments to be processed and distributed in real time. For example, as shown with respect to FIG. 2, data may be collected from network devices that may include devices within the internet of things, such as devices within a home automation network. However, such data may be collected from a variety of different resources in a variety of different environments. In any such situation, embodiments of the present technology allow for real-time processing of such data.

Aspects of the current disclosure provide technical solutions to technical problems, such as computing problems that arise when an ESP device fails which results in a complete service interruption and potentially significant data loss. The data loss can be catastrophic when the streamed data is supporting mission critical operations such as those in support of an ongoing manufacturing or drilling operation. An embodiment of an ESP system achieves a rapid and seamless failover of ESPE running at the plurality of ESP devices without service interruption or data loss, thus significantly improving the reliability of an operational system that relies on the live or real-time processing of the data streams. The event publishing systems, the event subscribing systems, and each ESPE not executing at a failed ESP device are not aware of or effected by the failed ESP device. The ESP system may include thousands of event publishing systems and event subscribing systems. The ESP system keeps the failover logic and awareness within the boundaries of out-messaging network connector and out-messaging network device.

In one example embodiment, a system is provided to support a failover when event stream processing (ESP) event blocks. The system includes, but is not limited to, an out-messaging network device and a computing device. The computing device includes, but is not limited to, a processor and a computer-readable medium operably coupled to the processor. The processor is configured to execute an ESP engine (ESPE). The computer-readable medium has instructions stored thereon that, when executed by the processor, cause the computing device to support the failover. An event block object is received from the ESPE that includes a unique identifier. A first status of the computing device as active or standby is determined. When the first status is active, a second status of the computing device as newly active or not newly active is determined. Newly active is determined when the computing device is switched from a standby status to an active status. When the second status is newly active, a last published event block object identifier that uniquely identifies a last published event block object is determined. A next event block object is selected from a non-transitory computer-readable medium accessible by the computing device. The next event block object has an event block object identifier that is greater than the determined last published event block object identifier. The selected next event block object is published to an out-messaging network device. When the second status of the computing device is not newly active, the received event block object is published to the out-messaging network device. When the first status of the computing device is standby, the received event block object is stored in the non-transitory computer-readable medium.

According to embodiments discussed herein, the above-described systems may be utilized to process historical events and perform modeling operations to generate probabilities of occurrence for events. These probabilities may be used to indicate a likelihood of whether an event actually occurred or an event may occur in the future. For example, systems discussed herein may assign a probability of occurrence to medical/pharmacy claim lines based on an individual's personal medical history and the experience of other patients in the same age/gender group. A low probability indicates that it would be unexpected to see the event given the individual's medical history and the history of others. The proposed technique will also provide specific details about how the presence or absence of selected medical events within particular time periods affected the probabilities. The assignment of the probabilities will serve two purposes: (1) it will help flag claims so that they can be reviewed for possible fraud prior; and (2) it has the potential to highlight when certain individuals are at risk of experiencing certain acute events so that early interventions and programs can be targeted to those most likely to benefit.

The proposed computerized approach, using systems discussed herein, allows the estimated probabilities to reflect a wide variety of previous medical histories. This includes medical and facility procedures, diagnoses, medications, places of service, places of residence, etc. Since several different procedure, diagnosis, and medication codes typically can be used to describe the same event, the systems discussed herein may achieve processing gains by grouping fifty-thousand or more codes into about thousand-two thousand (1,000-2,000) unique medical history events, for example. In addition, the model accounts for the fact that some events would be expected in different time periods relative to the event being modeled—for example, one medical event might be expected to occur within thirty (30) days prior to the event being modeled, while other medical events might be expected to occur within one (1) year prior to the event.

The proposed technique takes a unique approach in that the medical history of those who had the event is compared with the medical history of those who did not have the event. This allows for a more informative look at the medical history associated with the given event. Initially, a system may run models for each event for which a probability is desired, which may be stored in one or more storage systems including computerized storage devices. After those models have been built, however, computations and processing can be made in a real-time or near real-time fashion as the parameter estimates from the initial model, which may be retrieved from a storage system, runs can simply be used to assign probabilities to new claim lines. This has the potential to allow for a robust, informed approach to flagging medical claims associated with events for review before payment is made for those services. In addition, with the models in place, it would also be possible to predict which events a particular member is likely to experience in the near future, as well as which members are most likely to experience a specific acute event.

Moreover, the system allows for the real-time determination of whether a medical claim is consistent with prior information available for the patient. These real-time determinations cannot occur without the systems discussed herein. For example, a person could not compute the results discussed herein by hand because the amount of information to process is too much for a person to compute in a reasonable and sufficient amount of time to detect fraud before it occurs. Moreover, the real-time distributed nature of the systems and processing discussed herein solves these large data processing problems.

The proposed technique also takes into account the experience of this individual as well as other individuals of the same age, gender and prior eligibility period, provides specific details related to why a claim does not appear correct (via a decision tree data structure), and provides the potential for the client to select certain parts of a tree for immediate flagging and review. These decision tree data structures may be presented to a user on a display device to enable a user to interact with via one or more inputs. Thus, a user may interactively "drill down" on the select parts of the tree using these inputs and presentations.

Once all models are run, a probability and relative risk would be available for a percent (e.g., 90-95%+) of claim lines filed, which allows for the comparison of providers on a consistent scale and has the potential to more easily highlight suspect providers. For example, one provider might tend to have lower probabilities/relative risks indicating their patients likely did not need all of the services they received (or that they were not actually rendered). The system allows clients to determine those with the highest probability of experiencing a particular acute event. It can also do the following, suggest individuals to be enrolled in specific programs or interventions, and determine which patients might be candidates for particular medications.

In one particular example, systems and techniques discussed herein may include obtaining medical event history information for patients, the medical event history information includes medical history events. The system and techniques also include determining a particular medical event to determine a probability of occurrence based on a presence or absence of medical history events at specific prior time periods. The particular medical event may be obtained or determined in real-time or near real-time when a claim is filed and associated with the event. In some instances, the particular medical event may be associated with a claim that has been previously filed. Further, the particular medical event may be chosen to determine whether a subject may experience the event, based on a probability of occurrence, at some future point in time. Embodiments are not limited in this manner.

In some embodiments, the system and techniques include selecting, at random, one medical event per subject for subjects having experienced the particular medical event for inclusion in a set of medical events to be modeled. Further, the system and techniques also include selecting, at random, one medical event per subject for subjects having not experienced the particular medical event for inclusion in the set of medical events to be modeled, each of the medical events selected for subjects having not experienced the particular medical event having a same seasonality as the medical events selected for subject having experienced the particular medical event.

In embodiments, the system includes generating a model based on the set medical history events for subjects having experienced the particular medical event and having not experienced the particular medical event, the model includes a decision tree having nodes corresponding with medical history events from the set of medical history events, each of the decision tree nodes having an indication of a probability of occurrence for the particular medical history event based on whether the corresponding medical history event of the node occurred or did not occur within a specific time period. As previously discussed the model and decision tree may be used to detect fraudulent claims based on a likelihood or probability of occurrence for the particular medical history event modeled. Further, presenting the decision tree having the nodes on a display enables a user to analyze particular aspects of the decision tree. These and other details are discussed in more detail herein.

Figure 11A:
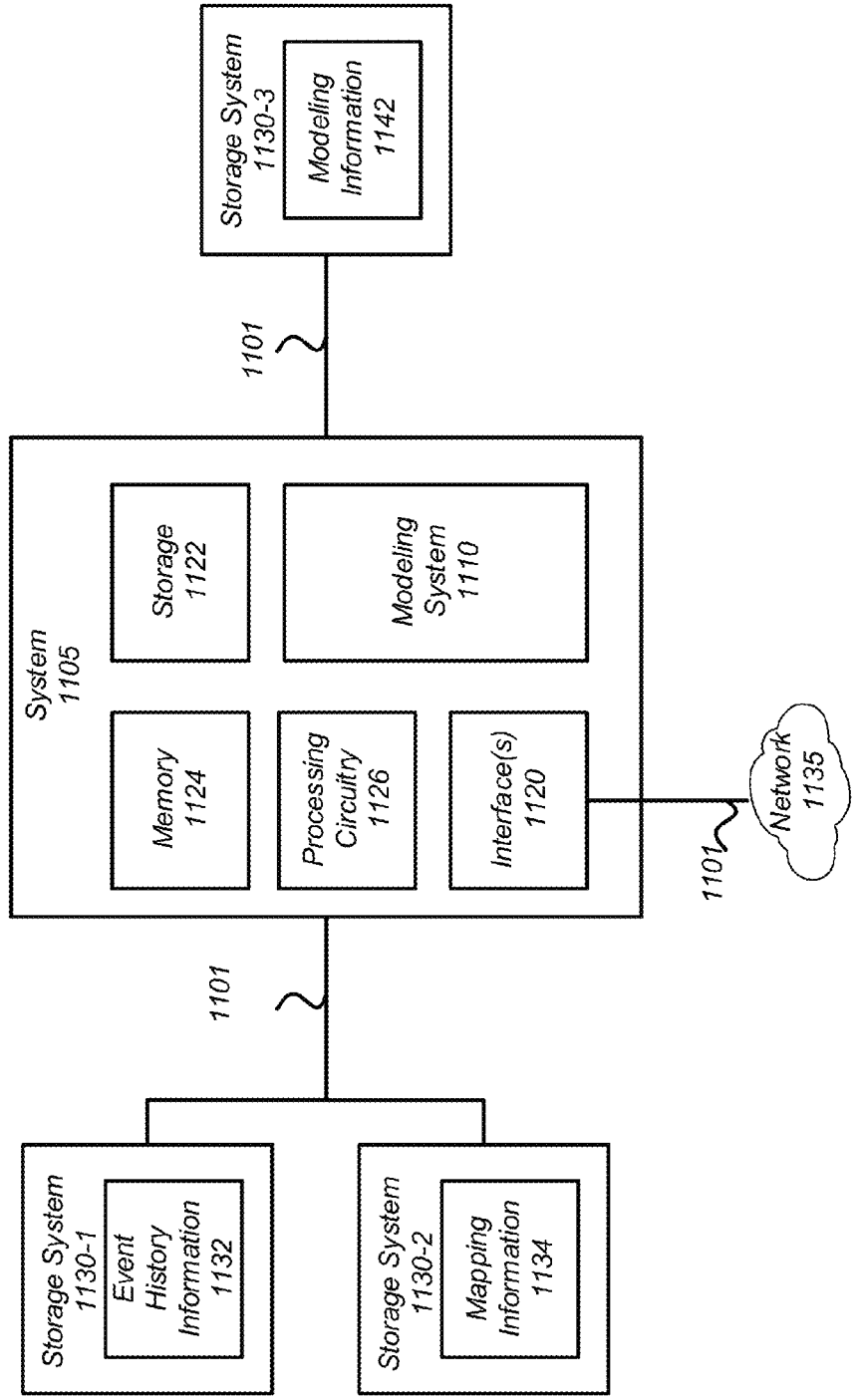
FIGS. 11A/11B/11C illustrate computing systems to process events and perform modeling operations, according to embodiments of the present technology.

FIGS. 11A/11B/11C illustrate examples of a computing system environment 1100 to process historical events and perform modeling operations to indicate a probability of occurrence of events based on the historical events. In embodiments, these operations may be performed in real-time or near real-time by the computing system environment 1100. Further, the illustrated computing system environment 1100 includes a number of systems, components, devices, and so forth to perform these operations; however, embodiments are not limited in the manner. In some embodiments, the computing system environment 1100 may include more or less systems, components, and devices, for example.

In some embodiments, the computing system environment 1100 may include a system 1105 having a number of components and may be coupled with a number of storage systems 1130-1 through 1130-4. Each of the storage systems 1130-1 through 1130-4 may include a number of networking elements, as discussed above, and may be coupled with system 1105 via one or more wired and/or wireless links 1101. Further, the storage system 1130-1 through 1130-4 may include any number of storage devices to store information and data, such as event history information 1132, mapping information 1134, and modeling information 1142. The information and data may be stored in any type of data structure, such as databases, lists, arrays, trees, hashes, files, and so forth. Further, a storage system 1130 may be a Network-attached storage (NAS), Direct-attached storage (DAS), a Storage area network (SAN), include storage devices, such as magnetic storage devices and optical storage devices. A storage system 1130 may also include volatile and non-volatile storage. Embodiments are not limited in this manner.

System 1105 also includes a number components, including, but not limited to, storage 1122, memory 1124, processing circuitry 1126, and one or more interfaces 1120. The system 1105 may be coupled with one or more other systems, components, devices, networks, and so forth through network environment 1135.

Storage 1122 may be any type of storage, including, but not limited to, magnetic storage and optical storage, for example. In some instances, storage 1122 may be part of one or more of the storage systems 1130-1 through 1130-4 and may be a DAS, NAS, or SAN. The storage 1122 may store information and data for system 1105, such as information for processing by the by the system 1105. In embodiments, the storage 1122 may store information, data, one or more instructions, code, and so forth for the modeling system 1110. Embodiments are not limited in this manner.

The memory 1124 of system 1105 can be implemented using any machine-readable or computer-readable media capable of storing data, including both volatile and non-volatile memory. In some embodiments, the machine-readable or computer-readable medium may include a non-transitory medium. The embodiments are not limited in this context. The memory 1124 can store data momentarily, temporarily, or permanently. The memory 1124 stores instructions and data for system 1105, which may be processed by processing circuitry 1126. For example, the memory 1124 may also store temporary variables or other intermediate information while the processing circuitry 1126 is executing instructions. The memory 1124 is not limited to storing the above discussed data; the memory 1124 may store any type of data.

In embodiments, the system 1105 may include processing circuitry 1126 which may include one or more of any type of computational element, such as but not limited to, a microprocessor, a processor, central processing unit, digital signal processing unit, dual core processor, mobile device processor, desktop processor, single core processor, a system-on-chip (SoC) device, complex instruction set computing (CISC) microprocessor, a reduced instruction set (RISC) microprocessor, a very long instruction word (VLIW) microprocessor, or any other type of processing circuitry, processor or processing circuit on a single chip or integrated circuit. The processing circuitry 1126 may be connected to and communicate with the other elements of the system 1105 including the modeling system 1110, the storage 1122, the memory 1124, and the one or more interfaces 1120.

The system 1105 may also include one or more interfaces 1120 which may enable the system to communicate over the network environment 135. In some embodiments, the interfaces 1120 can be a network interface, a universal serial bus interface (USB), a Firewire interface, a Small Computer System Interface (SCSI), a parallel port interface, a serial port interface, or any other device to enable the system 1105 to exchange information.

The system 1105 may also include a modeling system 1110 to perform real-time analytics using information, such as event history information 1132, to model the probability of occurrence of one or more events. For example, the modeling system 1110 can provide specific details of how the presence or absence of selected historical events within a particular time period affects the probability of occurrence of an event. The determination of the probability may be advantageous to a user of the system 1105 to determine whether the event or a claim associated with the event is fraudulent, for example. Further, the modeling system 1110 may be used to determine the probability of an event occurring in the future based on the historical event information.

Figure 11B:
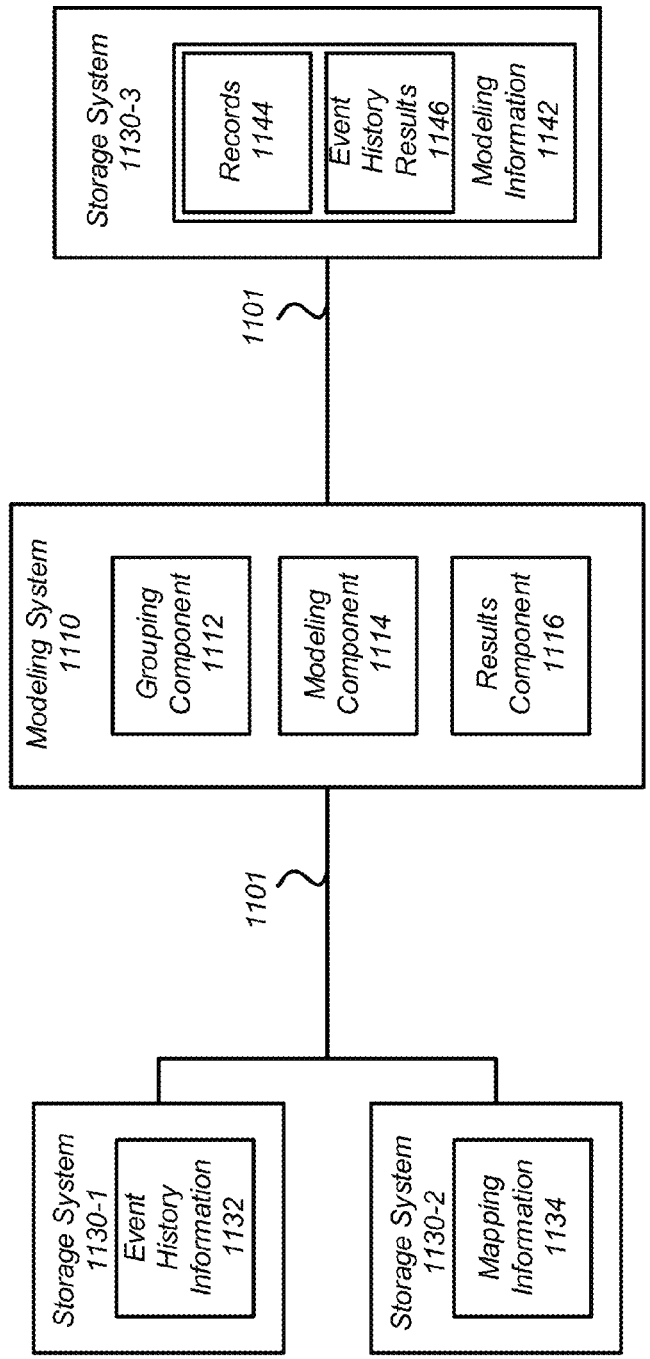

FIG. 11B illustrates an example of the computing system 1100 including the modeling system 1110 having a number of components and coupled with a number of storage systems 1130-1 through 1130-4. As previously discussed, each of the storage systems 1130-1 through 1130-4 may store information and data. For example, storage system 1130-1 may include event history information 1132, storage system 1130-2 may include mapping information 1134, storage system 1130-3 may include modeling information 1142 including records 1144 and event history results 1146, and storage system 1130-4 may include events 1127. Embodiments are not limited in this manner. Further and although computing system 1100 includes four storage systems 1130-1 through 1130-4, embodiments may include any number of storage system 1130. In some instances, computing system 1100 may include only a single storage system 1130, for example.

In embodiments, the modeling system 1110 may include a number of components, such as a grouping component 1112, a modeling component 1114, and a results component 1116 to model historical events and determine probabilities of occurrence of events based on historical events. The modeling results may also be presented to a user in a presentation on a display device.

In embodiments, the grouping component 1112 may receive or retrieve the event history information 1132 from the storage system 1130-1 and group the information based on relationships or associations defined in the mapping information 1134 in storage system 1130-2. The grouped information may be used by the modeling component 1114 to generate records 1144 which may include samples from the event history information 1132. The records 1144 may be used by the results component 1116 to generate modeled results 1151 for presentation on a display device, for example.

Figure 12:
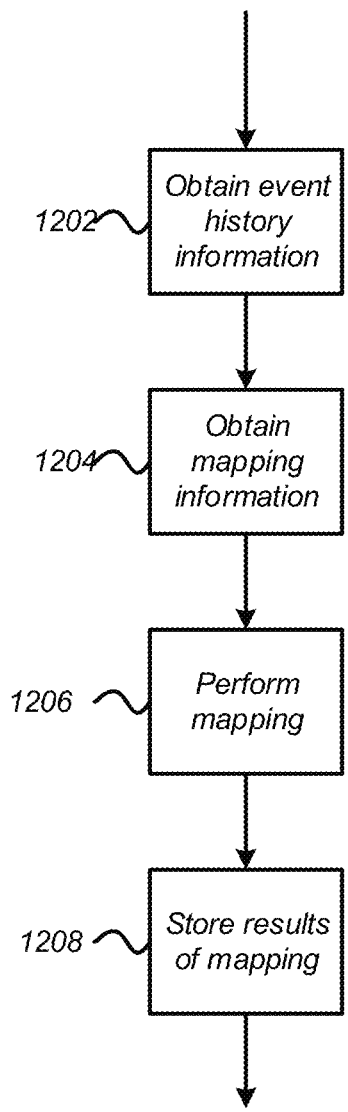
FIG. 12 illustrates an example logic flow to process event history information.

FIG. 12 illustrates one possible logic flow 1200 that may occur during operation of a grouping routine performed by the components of the modeling system 1110, such as the grouping component 1112, to reduce the number of codes describing events. At block 1202, the logic flow 1200 may include obtaining event history information 1132. In some embodiments, the event history information 1132 may include medical event history information for one or more subjects or patients. For example, the event history information 1132 may include claim codes to describe events, such as medical procedure, medical diagnoses, medication, place of service, place of residence, etc. The event history information 1132 may also include subject identifiers to identify each subject, and event dates (medical history event dates) for each event associated with the one or more subjects. In some instances, a single event may be described using more than one claim code, for example. Thus, embodiments may include reducing the number of claim codes that can describe the same event using the mapping information 1134. By reducing the number of claim codes that are describing the same event, the modeling system 1110 may process and model results more quickly by using less processing cycles and memory.

At block 1204, the logic flow 1200 may include obtaining mapping information 1134 which may be used to reduce the number of claim codes available to describe events and to map the claim codes to events. The mapping information 1134 includes mappings of claim codes to other, group or parent claim codes, for example. A raw or global set of claim codes may include more than sixty thousand codes, for example, and these may be mapped and reduced to approximately fourteen hundred claim codes. For example, the mapping information 1134 may include National Drug Code (NDC) claim codes mapped to the first three characters of their Hierarchical Ingredient Code (HIC-3) claim codes, procedure codes may be mapped to their Clinical Classification Software (CCS) procedure group, diagnosis claim codes may be mapped to their International Classification Diseases $9^{th}$ Revision (ICD-9) claim codes, and so forth. The mapping information 1134 may also include alternative spellings of names for places or locations of service mapped to a common name.

At block 1206, the logic flow 1200 may include performing a mapping of the claim codes in the event history information 1132 to generate event history results 1146. The mapping may include reducing the total number of claim codes by grouping claim codes for the same event under a group claim code or a single claim code that may be used to describe a single event. In some instances, the modeling system 1110 may determine that claim codes are for a single event based on an indicated date of occurrence, a common group claim code, or both. Embodiments are not limited in this manner.

The event history results 1146 may be stored in storage, such as a storage system 1130-3, at block 1208. In some instances, the event history results 1146 may be stored in a database and in a database format, in one or more files and file format, or any other data structure for storing information. The event history results 1146 may include a subject identifier for each subject, an event identifier (e.g. claim code) for each event, a date a claim was submitted or filed, and a date of a last occurrence of an event. The event history results 1146 may include events for all types of medical claims data, including but not limited, professional claims, facility claims, pharmaceutical claims, home health/long-term care (LTC) claims, etc. Note that while the number of claim codes may be reduced and medical history is tracked at a high level (group claim code) in the event history results 1146, a model to determine a probability of occurrence of an event is generated based on a submitted or filed claim code. Further, the event history results 1146 may be retrieved by the modeling system 1110 to perform real-time modeling when a new claim is filed, for example. The stored event history results 1146 may be quickly retrieved to perform the real-time modeling and determine a probability of occurrence of the event associated with the claim. As will be discussed in more detail in the following description, once the event history results 1146 are stored and available to look up for a given claim or event, models to assign a probability and determine relative risk for each event may be generated.

Although FIG. 12 illustrates certain blocks occurring in a particular order, various embodiments are not limited in this manner. For example, one or more blocks may occur in parallel or simultaneously. In another example, one or more blocks may occur before or after other blocks and may be in a different order. Also, the blocks are not dependent upon one another.

In some embodiments, the modeling system 1110 may include a modeling component 1114 to determine and generate records 1144 that may be used to generate models. As discussed, the models may be used to determine a probability of occurrence for events that may have already occurred and are incorporated into the event history results 1146 or new events as they occur in real-time or near real-time, e.g., when a new claim code is filed or submitted. The records 1144 may include samples of event history information 1132 selected from subjects that have and have not experienced an event based on one or more category parameters, including gender, age, and eligibility associated with the event modeled. More specifically, each sample may include a randomly chosen claim for each subject that is in the same gender category, age category, and eligibility category associated with the subject having the event modeled.

Figure 13:
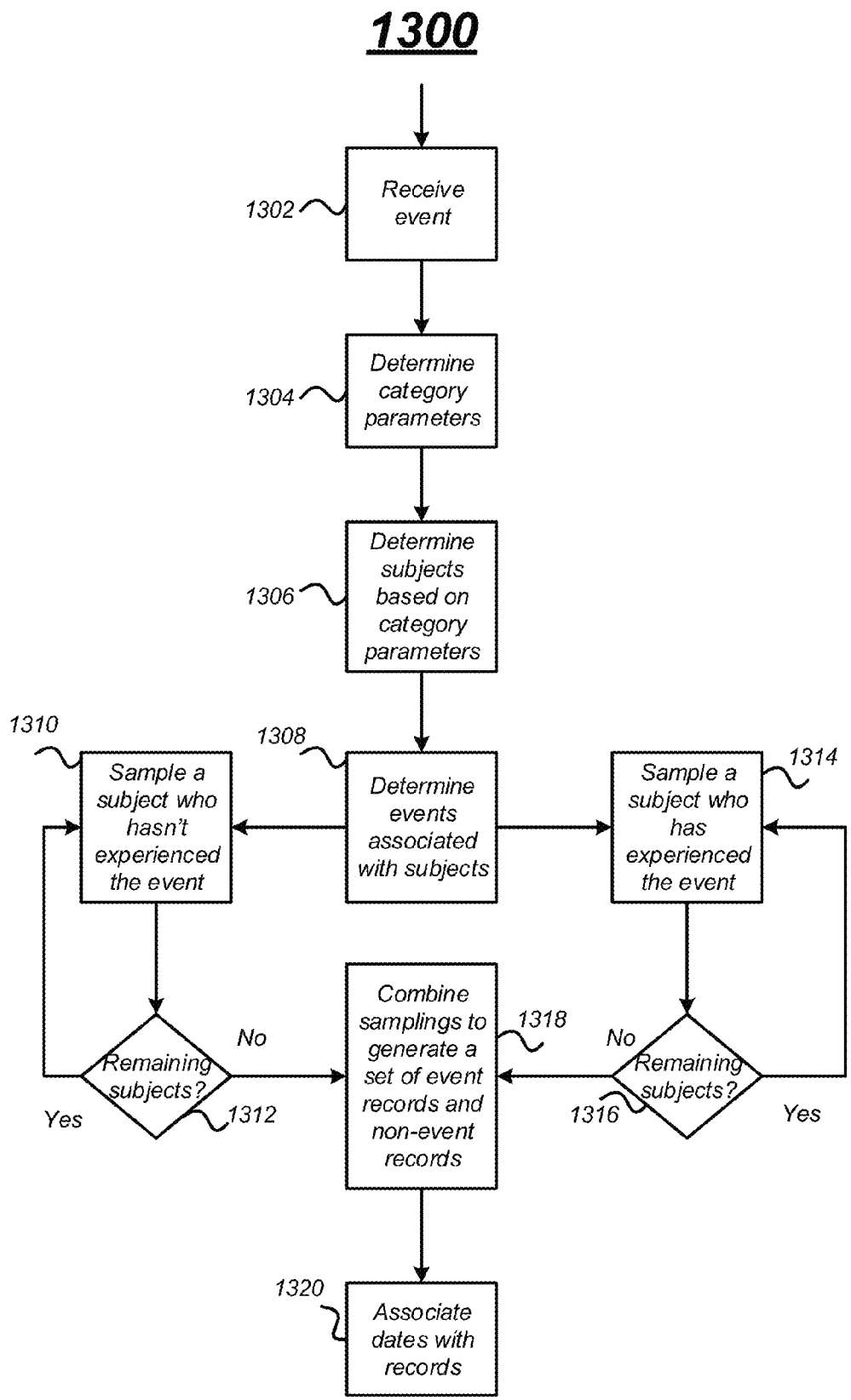
FIG. 13 illustrates an example logic flow to process event history information and generate records for use in creating models.

FIG. 13 illustrates one possible logic flow 1300 for generating records 1144 for use in generating a model to determine a probability of occurrence for events by components of the modeling system 1110, such as the modeling component 1114. Reference is made to FIG. 13.

Figure 11C:
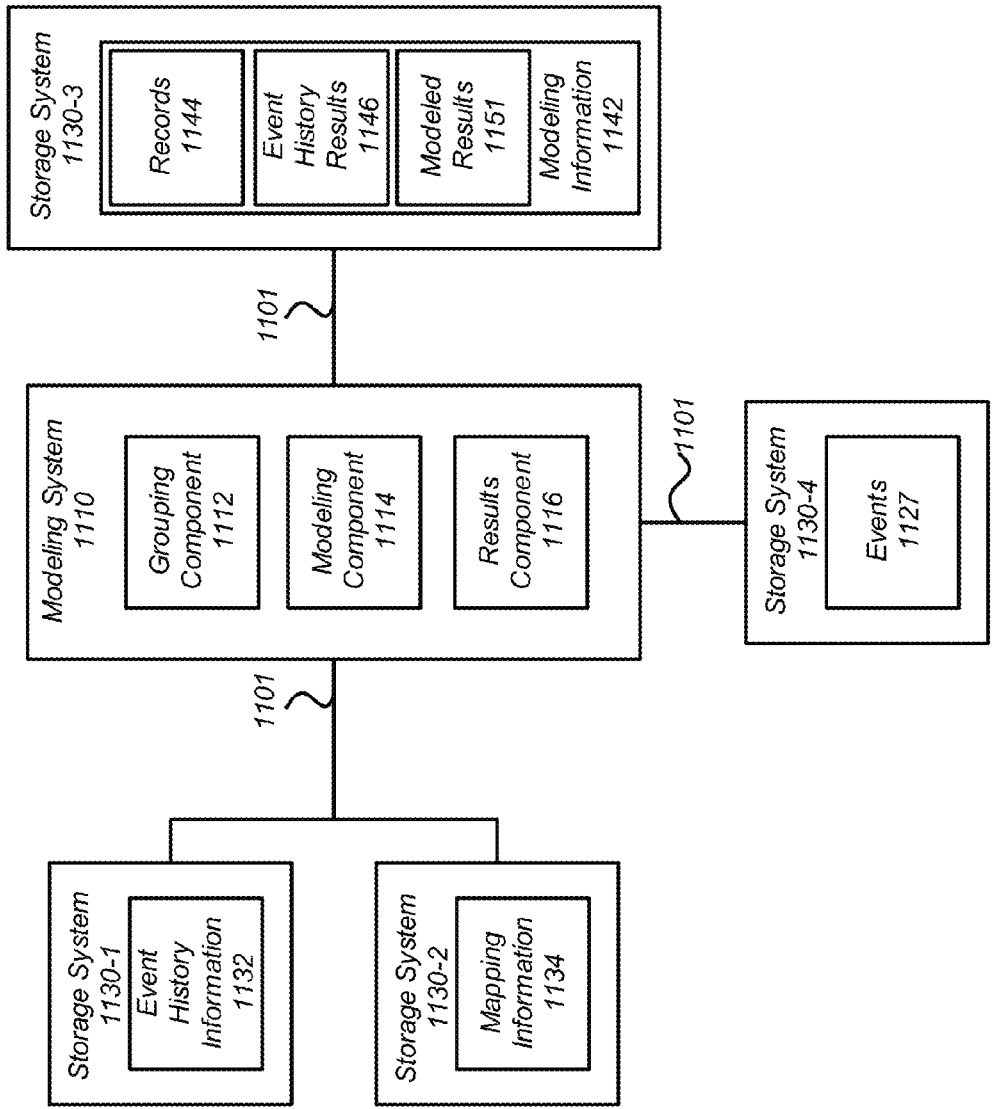

At block 1302, the logic flow 1300 may include obtaining an event, such as one of the events 1127 from storage system 1130-4 as illustrated in FIG. 11C. The event may be chosen to generate a model to determine a probability of occurrence. In some instances, the event is received by the modeling system 1110 from another system, such as a healthcare system, when a claim is filed, e.g., in real-time or near real-time to detect potential fraud before money is distributed to pay for the event. In some instances, the event may be one of the events from the event history information 1132. For example, a user may desire to perform an audit to detect any potential fraud on claims previously filed. The event may also be associated with identification information (a claim code), a date of occurrence, a date of filing of the claim code, and a subject identifier to identify a subject associated with the event. This information may be communicated to the modeling system 1110 with the event or retrieved from another system.

At block 1304, category parameters for the event to be modeled may be determined. The category parameters may include age, a gender, and an eligibility category for a subject associated with the event. Since subjects of different genders and ages are likely to experience different events, a different model may be generated based on these different category parameters. The age category parameter may be defined as a range of ages, e.g., from zero-eighteen months, eighteen months-three years old, three years old-twelve years old, thirteen years old-eighteen years old, and so on. The age groupings may be predetermined, computer determined, user configured, and so forth.

In some embodiments, since each subject may be eligible for different periods of time and have experienced a different number of events, an eligibility parameter may be determined. A subject that has been eligible for longer periods of time would have a chance to experience more events than a subject that has not been eligible for as long of a period. In one example, there may be four eligibility categories, events that occur: within one month, within three months, within six months, and within one year of the event modeled. However, embodiments are not limited in this manner and a different number of eligibility categories having different periods of time may be defined and computer generated.

The eligibility category may be used to determine how much information is available for a subject. For example, if a subject just obtained medical coverage, then the system would expect less or no information for the subject. However, if the subject has had their medical coverage for a number of years, then the system would expect more information which may include a number of events leading up to the event modeled. Thus, a separate model may be generated for subjects that have less than (<3) months of eligibility versus subjects that have a number of years of eligibly because of the differences in the amounts of information available, for example.

The logic flow 1300, at block 1306, may include determining subjects having the same category parameters as the subject of the event modeled. The subjects may be determined from the subjects having information in the event history information 1132. The total number of subjects in the event history information 1132 may be reduced to subjects having the same category parameters for each event modeled and different subjects may be chosen based on the event modeled. For example, an event modeled, as determined at block 1302, may be for a subject that is a male, between the ages of thirty and thirty-five, and has an eligibility category of within one year. Subjects and their events having the same category parameters may be determined and chosen from the event history information to produce a model and assign a probability for the event. Different subjects for a different event may be chosen based on the category parameters associated with the event modeled.

At block 1308, the logic flow 1300 may include determining each event, e.g., claim code, for each of the subjects that were determined to have the same category parameters at block 1306. These events may be determined based on subject identifiers and other identifiers specifying each category parameter for the events in the event history information 1132. The subject identifiers may also link each of the subjects to the events in the event history information 1132. The events may be divided into groups based on whether an associated subject experienced or did not experience the event modeled.

At block 1310, an event for a subject that has not experienced the event modeled and having the same category parameters, is selected at random from the events in the event history information 1132. A random event may be sampled for each subject that has not experienced the event being modeled and having the same category parameters, as indicated by decision block 1312 to determine whether any subjects that meet the category parameters remain for sampling. These events sampled for subjects who have not experienced the event modeled may be considered non-event records for modeling purposes.

Similarly, at block 314, an event for a subject that has experienced the event being modeled and having the same category parameters, is selected at random from the events associated with that subject. A random event may be sampled for each subject that has experienced the event being modeled and having the same category parameters, as indicated by decision block 1316 to determine whether any subjects that meet the category parameters remain for sampling. These events sampled for subjects who have experienced the event modeled may be considered event records for modeling purposes.

The logic flow 1300, at block 1318, includes combining the samples to generate a set of event records and non-event records to perform modeling and assign a probability of occurrence for the event. These event records and non-event records may be stored in storage, such as storage system 1130-3, as records 1144 for use in modeling. Thus, each event record and non-event record are combined such that the records 1144 include one record for each subject in the age, gender, eligibility group, for subjects who experienced and not experienced the event modeled. Further and at block 1320, each record 1144, e.g. event record and non-event record, may be associated with a date of a last occurrence of the event in the record. For example, the historical event results 1146 may be combined with the event and non-event records and used to determine the date of the last occurrence for each of the events. This information may be stored as the records 1144 in the storage system 1130-3. If a subject did not experience the event in the record 1144 before the date of service for the event modeled, the date field is left blank or a null value is entered in the date field. As will be discussed in more detail below, one or more models may be generated for the event and probability of occurrence may be assigned based on the model. Further, the operations discussed in FIG. 13 may be performed for each of the events in the event history information 1132 and models may be generated for each event to determine the probability of occurrences.

Although FIG. 13 illustrates certain blocks occurring in a particular order, various embodiments are not limited in this manner. For example, one or more blocks may occur in parallel or simultaneously. In another example, one or more blocks may occur before or after other blocks and may be in a different order. Also, the blocks are not dependent upon one another.

The records 1144 may be used to generate models for the event to determine a probability of occurrence. The models being generated may take into account information about the subject who experienced the event being modeled, including the subject's age and gender, their previously event history (medical history including procedures and diagnosis codes), the places that they received service, where they live (nursing home, assisted living, etc.), any other relevant information, and similar information about the other subjects in the event history information 1132. Further, relative times of events experienced by the subjects are also accounted for since events, such as medical events, typically occur in a related manner or sequence.

Figure 14:
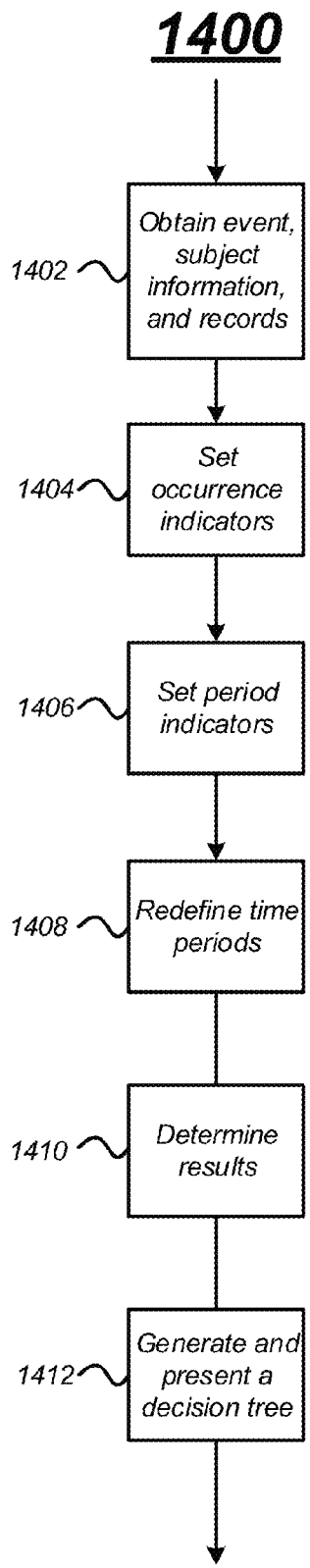
FIG. 14 illustrates an example logic flow to model an event using records and event history information.

FIG. 14 illustrates one possible logic flow 1400 to generate models and model results 1151 to assign probabilities of occurrence to events by components of the modeling system 1110, such as the results component 1116. Reference is made to FIG. 14.

At block 1402, the logic flow 1400 includes obtaining an event to be modeled, subject information, and records 1144. The event modeled may be an event 1127 in storage system 1130-4. In some instances, the event may be obtained in real-time or near real-time as a claim is filed associated with the event.

In embodiments, the subject information may be obtained from the event history information 1132 for the subject associated with the event modeled. For example, the subject information may include the medical history, such as claims filed, events experienced, medication taken, procedures performed, places of care, housing information, and so forth from the event history information 1132. The subject information may be obtained based on the eligibility category or available information for the subject. For example, the eligibility category for the subject may be events which have occurred within six months (>6 months) of the event modeled. In another example, the eligibility category for the subject may be events which have occurred within one month (>1 month) of the event being modeled. Embodiments are not limited in this manner and other eligibility periods may exist, e.g. within three months (>3 months), within nine months (>9 months), within twelve months (>12 months), etc. of the event being modeled. As discussed in more detail below; the eligibility category may be used to select the events experienced by the subject for modeling.

The records 1144 obtained may include the event records and non-event records, e.g., the samples events taken based on the event modeled as discussed in FIG. 13. Further, the records 1144 may also include other information, such as a date of occurrence of an event of the record and a subject identifier to identify a subject. In some instances, the records 1144 may also include category parameters for each of the subjects associated with an event. The records 1144 may also include a date of occurrence of the same event as the event modeled for the event records, e.g., records for subjects who experienced the event modeled. The records 1144 may include a blank or null value for non-event records for subjects who have not experienced the event.

At block 1404, one or more occurrence indicators may be set for each event in the records 1144, e.g., the non-event records and event records. The modeling system 1110, for example, may compare the events experienced by the subject listed in the subject information to determine whether the subject experienced each particular event in the records 1144 before the event being modeled. If the subject has experienced the event, a yes or one value may be set for the event in the records 1144 or a data structure associated with the records 1144. Similarly, if the subject has not experienced the event, a no or zero (null) value may be set for the event in the records 1144 or a data structure associated with the records 1144. Note that any value may be used to indicate yes and no values and embodiments are not limited in this manner.

At block 1406, period indicators may be set on each event in the records 1144 having an occurrence indicator indicating the subject experienced the event. The period indicators may indicate whether the subject experienced the event between a time range, e.g. period values. For example, a period indicator may indicate that the subject experienced the event between zero to one month, one month to three months, three months to six months, and six months to twelve months, etc. Embodiments are not limited in this manner. The period indicators may be set based on whether the subject experienced the event in the records 1144 during the eligibility period as defined by the eligibility category. For example, a subject may have experienced an event listed in the records 1144, but it may be outside of the eligibility period. In these instances, a no value may be set as a period indicator in the records 1144 for the event.

At block 1408, the period indicator for each event in the records 1144 may be adjusted to be relative to the date of occurrence of the event being modeled. For example, a period indicator may be adjusted to indicate that the subject experienced the event in the records 1144 less than one month before the event being modeled. In another example, a period indicator may be adjusted to indicate that the subject experienced the event in the records 1144 between one month and three months before the event being modeled. In a third example, a period indicator may be adjusted to indicate that the subject experienced an event in the records 1144 between three months and six months before the event being modeled. In a fourth example, a period indicator may be adjusted to indicate that the subject experienced the event in the records 1144 between six months and twelve months before the event being modeled. Embodiments are not limited to these examples. The period indicators may be used to isolate any significant events and time period combinations of events of the records 1144 and the event modeled.

At block 1410, the logic flow 1400 includes generating the modeled results 1151 to indicate and assign probability of occurrences of an event based on event records and non-event records in records 1144. As mentioned, these records 1144 take into account previous events experienced by a subject, events experienced by other subjects who have experienced the event being modeled, and events experienced by other subject who have not experienced the event being modeled, for example. Different predictive modeling algorithms may be used to generate the modeled results 1151. In one example, a tree-based approach partitions a population (subjects) and estimates probabilities. In another example, neural networks or regression algorithms estimate parameters based on an assumed parametric relationship. Based on the operations leading up to block 1410, a subpopulation has been selected (e.g. males age 40-50 who have at least one year of eligibility). Thus, the selected subpopulation has at least one year of history for the system to process. A first model (block 1404) may be generated for the entire period of eligibility (e.g. in this case 1 year) and based on whether a subject (yes/no) experienced an event as a function of the subjects whom have experienced the event (yes/no), one for each history event experienced by the subject for whom the event is being modeled. The result of this model (a decision tree data structure) is that we know the historical events that are related to the event being modeled. The second model (block 1406) does the same exact thing, except the system replaces each (yes/no) did they have a history event at all over the past year with one for each time period (<3 months, 3-6 months, 6-12 months), e.g. three in this example. So if the first model had ten history events, the second model has thirty events/time periods. The result of the second model is that the system knows the events and time periods that are for determining the probabilities of occurrence. The third model (block 1408) redefines the results of the second model to highlight different periods for a history event and easier for a user to read.

In some embodiments, the modeled results 1151 may indicate a probability of occurrence for an event indicated as having occurred to the subject. In some instances, the modeled results 1151 may also indicate a likeliness of occurrence of an event (based on a percentage) for subjects. The modeled results 1151 may also indicate the most likely events a subject may experience. The system 1100, for example, may select whether to generate a model for an event that has occurred, determine most likely events to occur, and determine likeliness of occurrence of a specific event, for example.

At block 1412, a decision tree may be generated and presented indicating the modeled results 1151 for a particular event. A decision tree may be directed to the event modeled and may include decision tree nodes (leaves) and branches. The decision tree nodes of the decision tree correspond with events in the event history information 1132 and sampled as the records 1144. Each decision tree node may include an indication of a probability of occurrence of the event being modeled based on whether the subject experienced or did not experience the event of the decision tree node. In some embodiments, the probability of occurrence may be based on whether the event in the decision tree node occurred within the eligibility period or specified time period, as indicated by the period indicators.

The branches of the decision tree may couple the decision tree nodes, and each of the branches may be generated based on the occurrence indicators and period indicators. More specifically, each branch may connect a parent decision tree node to child decision tree nodes based on whether a subject experienced the event associated with the parent decision tree node or not. For example, one branch of a parent decision tree node may be directed and lead to a first child decision tree node if the subject experienced an event of the parent. Another branch may be directed and lead to a second child decision tree node if the subject did not experience the event of the parent decision tree node. The probability of occurrence of the event being modeled is based on whether the subject experienced or did not experience the event of the parent decision tree node.

The decision tree may be presented to a user on a display device (not shown) which may be coupled to the system 1105. In some instances, the display device may be integrated into the system 1105 and in other instances, the display device may be remote to the system 1105. For example, the system 1105 may communicate a decision tree via one or more networks, such as network 1135, for presentation on a remote device. In some examples and as previously mentioned, the system 1105 may be a distributed system and perform assignments of probability of occurrences in real-time or near real-time. In these instances, a decision tree may be presented and updated in real-time as events 1127 and event history information 1132 are received by the system 1105.

Figure 15A:
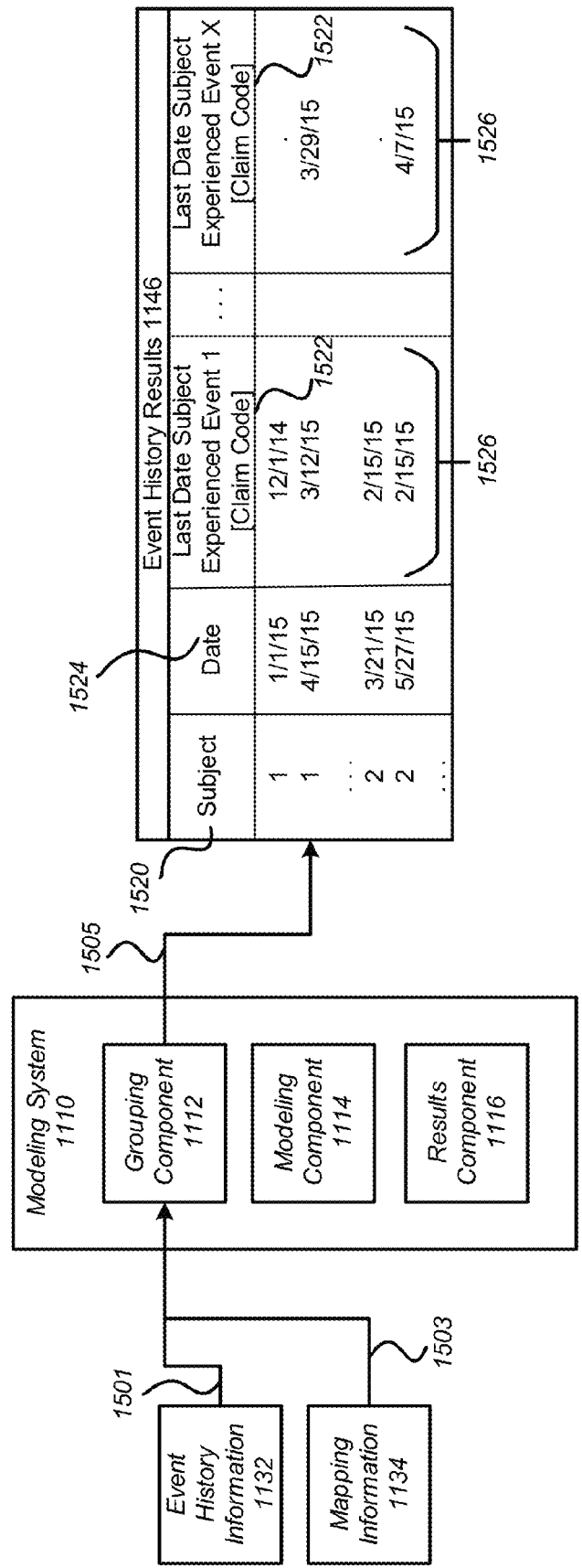
FIG. 15A illustrates an example processing flow to generate event history results.

FIG. 15A illustrates an example of a first processing flow 1500 to map codes to their parent codes and generate event history results 1146 from the event history information 1132.

At line 1501, the modeling system 1110 may obtain event history information 1132 which may include medical history for one or more subjects or patients. The event history information 1132 may include claim codes to describe events, for example. Further, the event history information 1132 may also include subject identifiers to identify each subject, and event dates for each event associated with the one or more subjects. In some instances, a single event may be described using more than one claim code, for example. Thus, embodiments may include reducing the number of claim codes that can describe the same event using the mapping information 1134.

At line 1503, the modeling system 1110 may obtain mapping information 1134 to reduce a number of claim codes available to describe events and to map the number of claim codes to a single event. As discussed, the mapping information 1134 includes mappings of claim codes to other, group claim codes, for example. In some embodiments, mapping information 1134 may include National Drug Code (NDC) claim codes mapped to the first three characters of their Hierarchical Ingredient Code (HIC-3) claim codes, procedure codes may be mapped to their Clinical Classification Software (CCS) procedure group, diagnosis claim codes may be mapped to their International Classification Diseases $9^{th}$ Revision (ICD-9) claim codes, and so forth. The mapping information 1134 may also include alternative spellings of names for places or locations of service mapped to a common name.

The modeling system 1110 may perform a mapping of the claim codes to reduce the number of claim codes that may apply to a single event. At line 1505, the modeling system 1110 may apply the reduced number of claim codes to the event history information 1132 to generate event history results 1146. The event history results 1146 may include a subject identifier 1520 for each subject, an event identifier 1522 (e.g. claim code) for each event, a filed date 1524 a claim was submitted or filed, and a last occurrence date 1526 of a last occurrence of an event. The event history results 1146 may include events for all types of medical claims data, including but not limited, professional claims, facility claims, pharmaceutical claims, home health/long-term care (LTC) claims, etc.

Figure 15B:
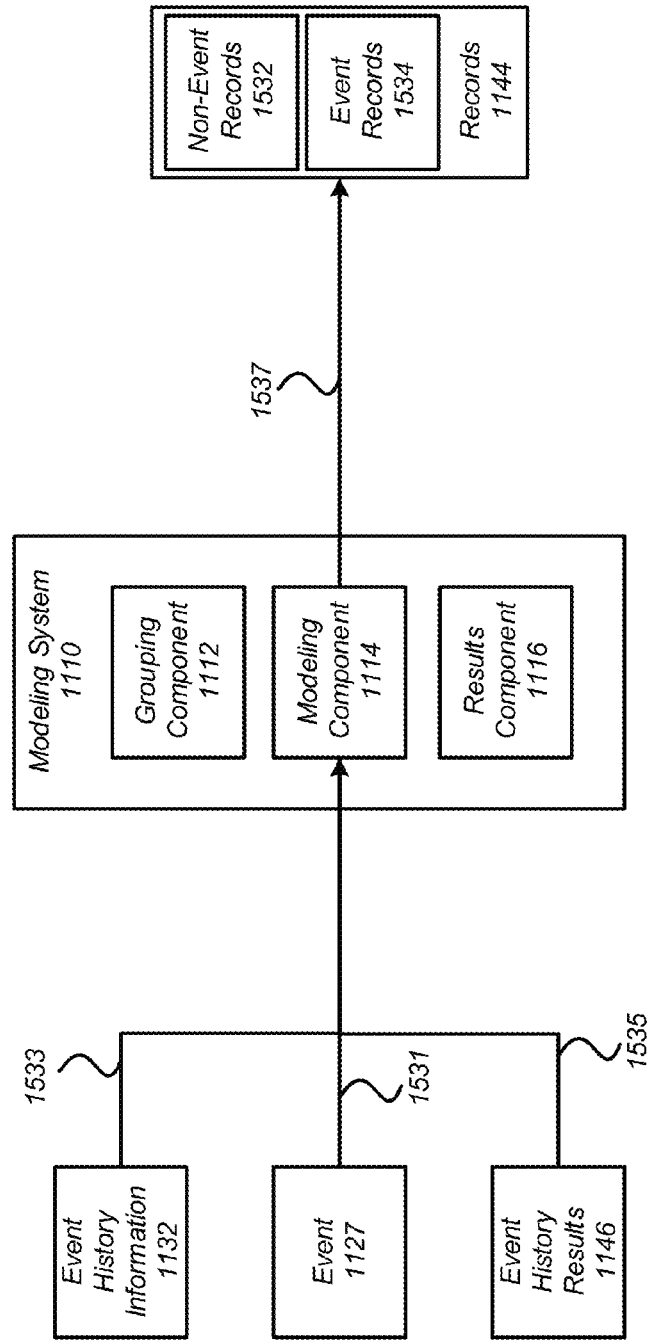
FIG. 15B illustrates an example processing flow to generate records.

FIG. 15B illustrates an example processing flow 1530 to process and generate records 1144 for use in modeling an event 1127 to determine a probability of occurrence and relative risk. At line 1531 the modeling system 1110 may obtain an event 1127 to model. As discussed, the event 1127 may be obtained in real-time or near real-time when a claim is filed. However, embodiments are not limited in this manner and the event 1127 may have occurred at some point in the past or for use in determining a likelihood of occurrence in the future, for example.

The modeling system 1110 may also determine category parameters for the event 1127. The category parameters may include age, a gender, and an eligibility category for a subject associated with the event 1127. The age may be defined as a range of ages, which may be predetermined, computer determined, user configured, and so forth. Also, since each subject may be eligible for different periods of time and have experienced a different number of events, an eligibility parameter may be determined. A subject that has been eligible for longer periods of time would have a chance to experience more events than a subject that has been eligible for a shorter period of time. In one example, there may be four eligibility categories, events that occur: within one month, within three months, within six months, and within one year of the event 1127 modeled. However, embodiments are not limited in this manner and a different number of eligibility categories having different periods of time may be defined and computer generated.

At line 1533, the modeling system 1110 may obtain the event history information 1132 and determine subjects having the same category parameters as the subject of the event 1127 modeled. In other words, the total number of subjects in the event history information 1132 may be reduced to subjects having the same category parameters, e.g. age, gender, and eligibility category, for each event modeled. For example, the subject associated with the event 1127 may be a male, between the ages of thirty and thirty-five, and has an eligibility category of within one year. The event history information 1132 may be analyzed and events associated with subjects having the same category parameters may be chosen to generate records 1144.

The events from the event history information 1132 for subjects having the same category parameters may be divided into groups based on whether a subject experienced or did not experience the event 1127 modeled. For example, events associated with subjects who have not experienced event 1127 may be grouped into one set of events. Events associated with subjects who have experienced event 1127 may be grouped into another set of events. Each of these sets of events may be sampled to generate the records 1144. For example, a random event may be sampled for each subject that has not experienced the event 1127 being modeled. Note that the events sampled are not the same event 1127 modeled. These events sampled for subjects who have not experienced the event modeled may be considered non-event records 1532.

Similarly events for a subject that has experienced the event 1127 modeled is selected at random from the events in the event history information 1132 associated with that subject. A random event may be sampled for each subject that has experienced the event being modeled and having the same category parameters. These events sampled for subjects who have experienced the event modeled may be considered event records 1534.

In embodiments, the modeling system 1110 may combine the samples to generate records 1144 including a set of event records 1534 and non-event records 1532 to perform modeling and assign a probability of occurrence for the event. Each event record 1534 and non-event record 1532 is combined such that the records 1144 include one record for each subject in the age, gender, and eligibility group, for subjects who experienced and did not experienced the event 1127 modeled.

At line 1535, each record 1144 may be associated with a date of a last occurrence of the event in the record 1144. For example, the historical event results 1146 may be combined with the event records 1534 and non-event records 1534 and used to determine the date of the last occurrence for each of the events. This information may be stored as the records 1144 in a storage system at line 1537. If the subject did not experience the event in the record 1144 before the date of service for the event 1127 modeled, the date is left blank.

Figure 15C:
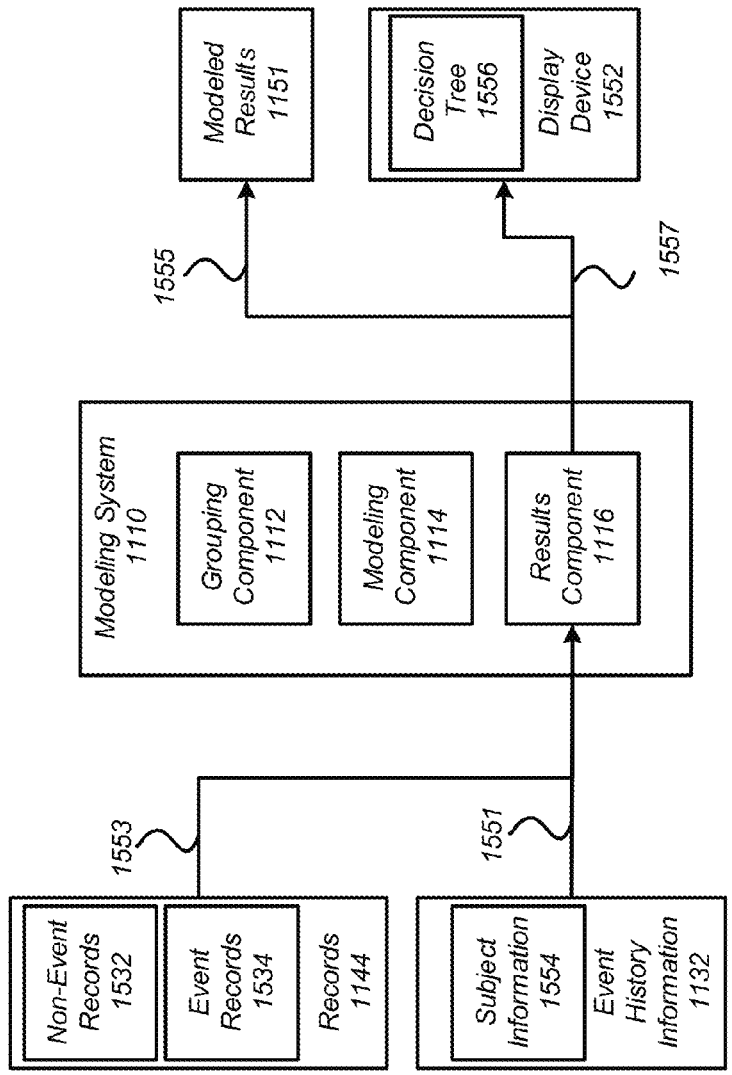
FIG. 15C illustrates an example processing flow to generate modeled results for presentation on a display device.

FIG. 15C illustrates an example processing flow 1550 to generate modeled results 1151 by the modeling 1110 for presentation on a display device 1552. The modeled results 1151 may be used to generate a decision tree for presentation, for example, which may illustrate a probability of occurrence and relative risk of an event based on the presence or absence of the events of the records 1144 during a specific time period.

At line 1551, the modeling system 1110 may obtain subject information 1554 and an event to be modeled. The subject information 1554 may be obtained from the event history information 1132 for the subject associated with the event modeled. For example, the subject information 1554 may include the medical history, such as claims filed, events experienced, medication taken, procedures performed, places of care, housing information, and so forth from the event history information 1132. The subject information 1554 may be obtained based on the eligibility category or available information for the subject. For example, the eligibility category for the subject may be events which have occurred within six months (>6 months) of the event modeled. In another example, the eligibility category for the subject may be events which have occurred within one month (>1 month) of the event being modeled. Embodiments are not limited in this manner and other eligibility periods may exist, e.g. within three months (>3 months), within nine months (>9 months), within twelve months (>12 months), etc. of the event being modeled. The eligibility category may be used to select the events experienced by the subject for modeling.

At line 1553, records 1144 may be obtained by the modeling system 1110. The records 1144 include the non-event records 1532 and the event records 1534 and may also include other information, such as a date of occurrence of an event of the record and a subject identifier to identify a subject. In some instances, the records 1144 may also include category parameters for each of the subjects associated with an event of the record 1144. The records 1144 may also include a date of occurrence of the same event as the event modeled for the event records, e.g. records for subjects who experienced the event modeled. The records 1144 may include a blank or null value for non-event records for subjects who have not experienced the event.

The modeling system 1110 may set one or more occurrence indicators for each event in the records 1144, e.g. the non-event records 1532 and event records 1534. For example, the modeling system 1110 may compare the events experienced by the subject in the subject information 1554 to determine whether the subject experienced each particular event in the records 1144 before the event modeled. If the subject has experienced the event, a yes or one value may be set for the event in the records 1144 or a data structure associated with the records 1144. Similarly, if the subject did not experience the event, a no or zero (null) value may be set for the event in the records 1144 or a data structure associated with the records 1144.

The modeling system 1110 may also set period indicators on each event in the records 1144 having an occurrence indicator. The period indicators may indicate whether the subject experienced the event between a time range. For example, a period indicator may indicate that the subject experienced the event between zero to one month, one month to three months, three months to six months, and six months to twelve months, etc. Embodiments are not limited in this manner.

Further, the modeling system 1110 may adjust the period indicator for each event in the records 1144 to be relative to the date of occurrence of the event modeled. For example, a period indicator may be adjusted to indicate that the subject experienced the event in the records 1144 less than one month before the event modeled. In another example, a period indicator may be adjusted to indicate that the subject experienced the event in the records 1144 between one month and three months before the event modeled. In a third example, a period indicator may be adjusted to indicate that the subject experienced an event in the records 1144 between three months and six months before the event modeled. In a fourth example, a period indicator may be adjusted to indicate that the subject experienced the event in the records 1144 between six months and twelve months before the event modeled. Embodiments are not limited to these examples. The period indicators may be used to isolate any significant events and time period combinations of events of the records 1144 and the event modeled.

At line 1555, the modeling system 1110 may generate modeled results 1151 to indicate and assign probability of occurrences of the modeled event based on the event records 1534 and non-event records 1532 in records 1144. As mentioned, these records 1144 take into account previous events experienced by the subject who experienced the event modeled, events experienced by other subjects who have experienced the event being modeled, and events experienced by other subject who have not experienced the event being modeled, for example.

Figure 16A:
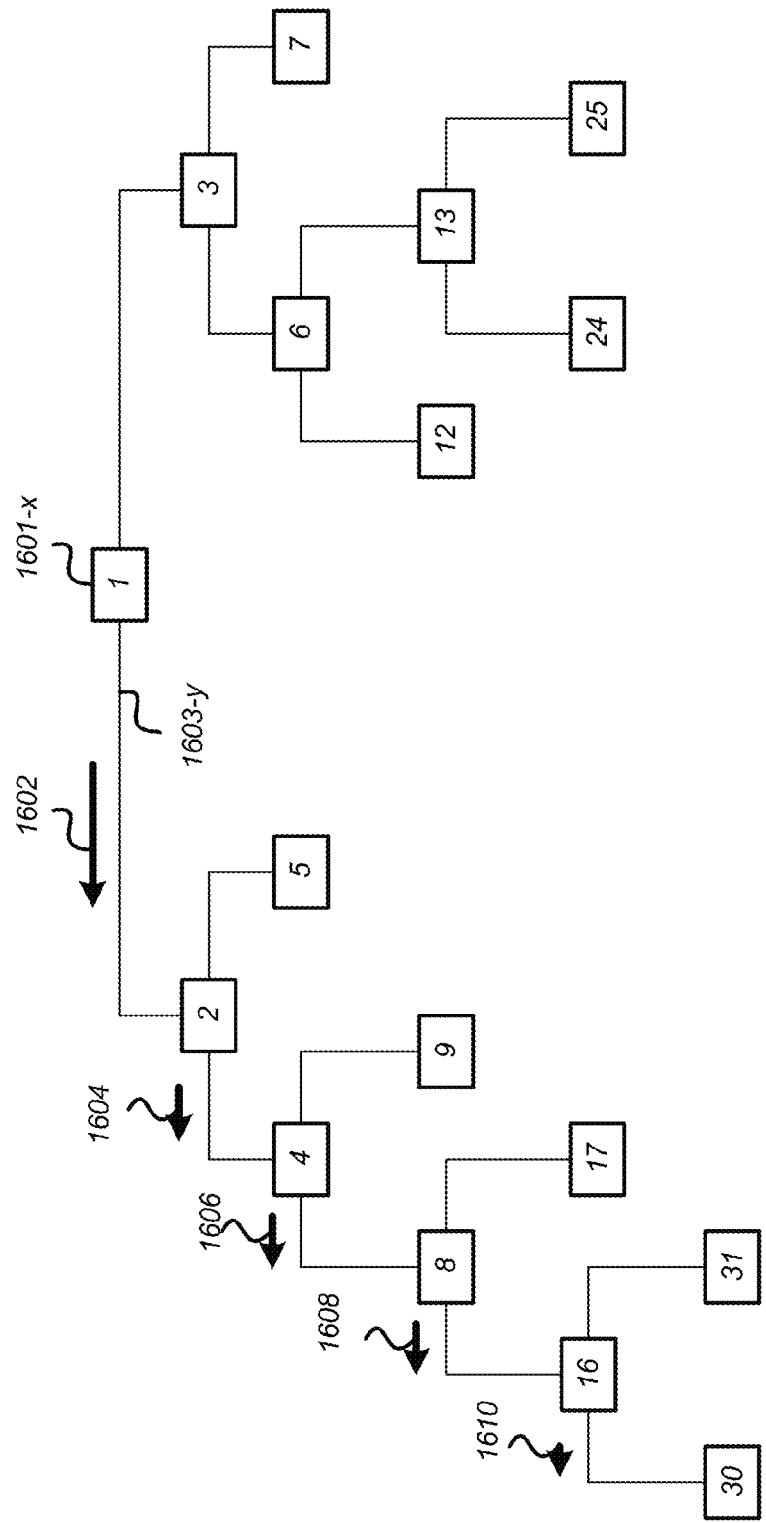
FIG. 16A illustrates an example presentation of a decision tree based on modeling of event.
Figure 16B:
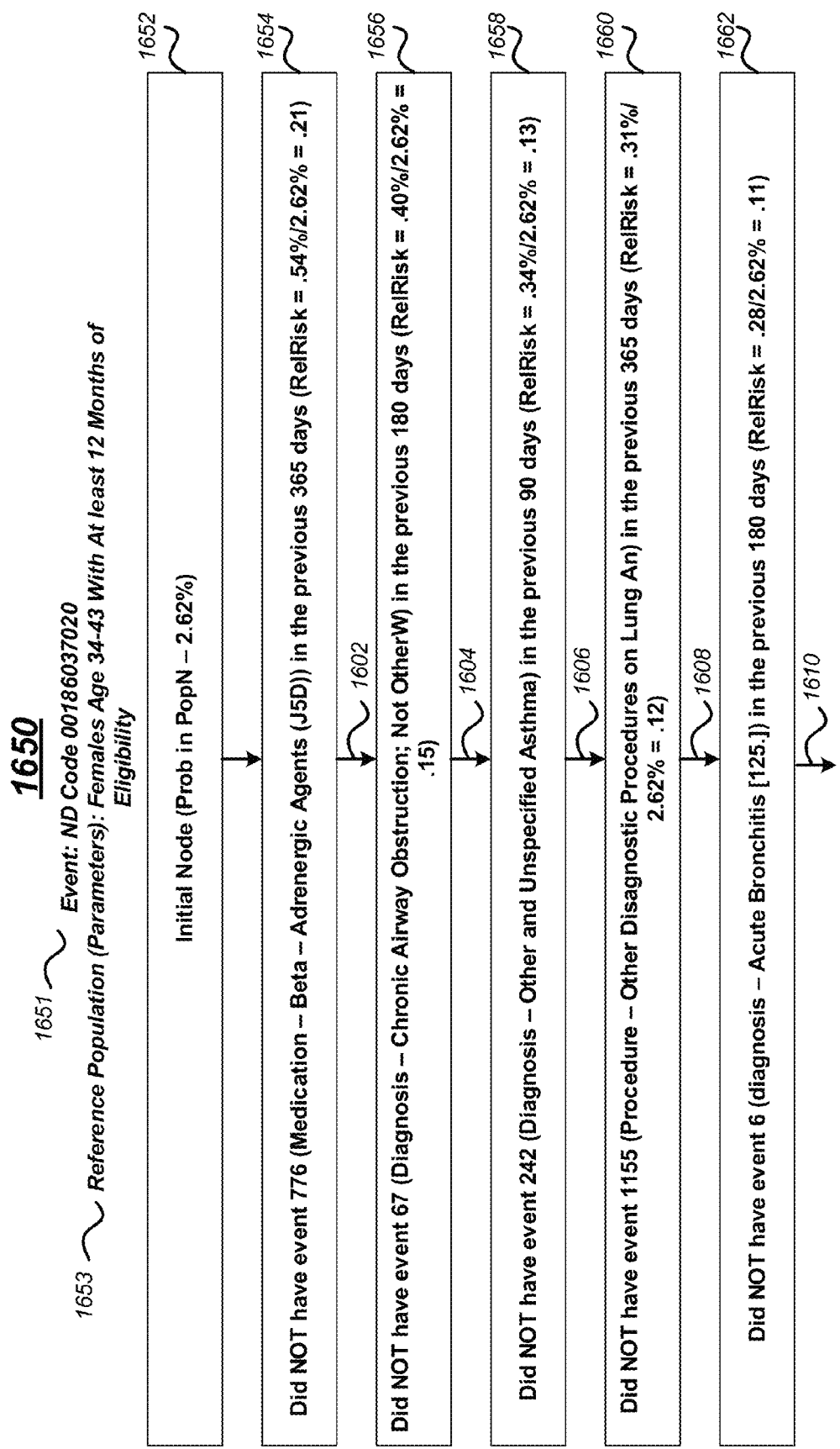
FIG. 16B illustrates detail information for the decision tree illustrated in FIG. 16A.

At lined 1557, the modeling system 1110 may generate a presentation, such as a decision tree to present on a display device 1552 for the event modeled. The decision tree may include decision tree nodes (leaves) and branches. FIGS. 16A/16B illustrate an example decision tree 1600 and corresponding probability and relative risk results 1650. Reference is now made to FIGS. 16A and 16B.

FIG. 16A illustrates an example decision tree 1600 having a plurality of decision tree nodes 1601-*x* and branches 1603-*y*, where x and y may be any positive integer. As previously discussed, each of the decision tree nodes 1601-*x* of the decision tree 1600 correspond with events in the event history information 1132 and sampled as the records 1144. Each decision tree node 1601-*x* may include an indication of a probability of occurrence of the event being modeled based on whether the subject experienced or did not experience the event of the decision tree node 1601-*x*, as illustrated in FIG. 16B. In some embodiments, the probability of occurrence may be based on whether the event in the decision tree node 1601-*x* occurred within the eligibility period or specified time period, as indicated by the period indicators.

The branches 1603-*y* of the decision tree 1600 may couple the decision tree nodes 1601-*x*, and each of the branches 1603-*y* may indicate whether the subject associated with the event modeled experienced or did not experience the event of the decision tree node 1601-*x*. More specifically, each branch 1603-*y* may connect a parent decision tree node 1601-*x* to child decision tree nodes 1601-*x* based on whether a subject experienced the event associated with the parent decision tree node or not. For example, one branch 1603-*y* of a parent decision tree node 1601-*x* may be directed and lead to a first child decision tree node 1601-*x* if the subject experienced an event of the parent. Another branch 1603-*y* may be directed and lead to a second child decision tree node 1601-*x* if the subject did not experience the event of the parent decision tree node 1601-*x*. The probability of occurrence of the event being modeled is based on whether the subject experienced or did not experience the event of the parent decision tree node 1601-*y*.

In the illustrated example of FIGS. 16A and 16B, a decision tree 1600 may be generated for the event having an event identification (claim code) 1651 of "00186037020" for a subject having category parameters 1653 of a female between the ages of thirty-four and forty-three with at least twelve month of eligibility, e.g. event history. At an initial decision tree node corresponding with block 1652 of FIG. 16B, the subject has a 2.62% chance of having the event modeled based on the event occurring within the general population.

At block 1 of FIG. 16A corresponding with block 1654, the subject did not experience the event (Medication-Beta) in the previous 365 days as indicated by the arrow 1602. In this case, since the subject did not experience the event of decision tree node 1, the probability of occurrence or relative risk of the subject experiencing the event modeled is reduced to 0.21. Similarly, the subject did not experience the event (Chronic Airway Obstruction) of decision tree node 2 of FIG. 16A corresponding with block 1656 of FIG. 16B in the previous 180 days as indicated by the arrow 1604. In this case, the relative risk for the event modeled is further reduced to 0.15.

At block 4 of FIG. 16A corresponding with block 1658 of FIG. 16B, the subject did not experience the event (Asthma) in the past 90 days, as indicated by arrow 1606. The relative risk for the event modeled is reduced to 0.13. The subject also did not experience the event (Procedure on Lung) of decision tree node 8 of FIG. 16A corresponding with block 1660 as indicated by arrow 1608. The relative risk of occurrence for the event modeled is further reduced to 0.13.

At block 16 of FIG. 16A corresponding with block 1662 of FIG. 16B, the subject did not experience the event (Acute Bronchitis) in the previous 180 days as indicated by arrow 1610. As such the relative risk of the subject experiencing the event modeled is further reduced to 0.11. FIGS. 16A and 16B illustrate one possible decision tree for modeling an event for a subject. A different decision tree may be generated for each event of the event history information 1132 or for new events as they are obtained. The process may be repeated for any number of events. Further, different models may be used to generate a different presentation. For example, once models have been generated for all of the events in the event history information 1132, the location associated with each event may be used to generate a "heat" or "fraud" map. The fraud map may show areas or higher concentration and lower concentration of claims being filed in locations. Thus, a user may be able to determine the location of a fraudulent doctor writing more than a statistically significant amount prescriptions, for example. Embodiments are not limited in this manner.

Figure 17A:
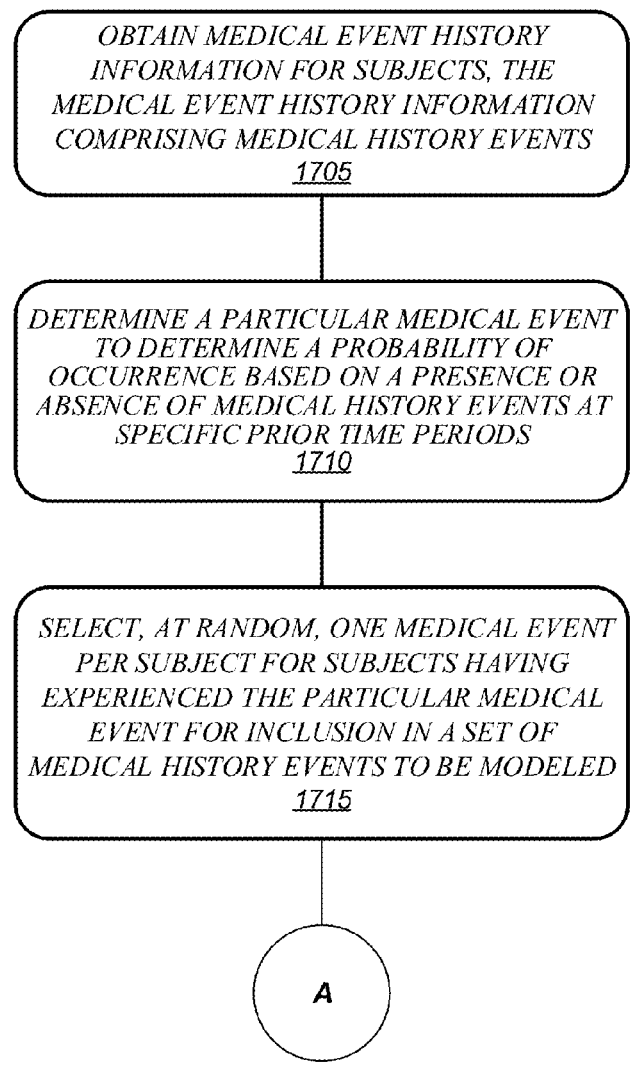
FIGS. 17A/17B illustrate an example logic flow to process information.
Figure 17B:
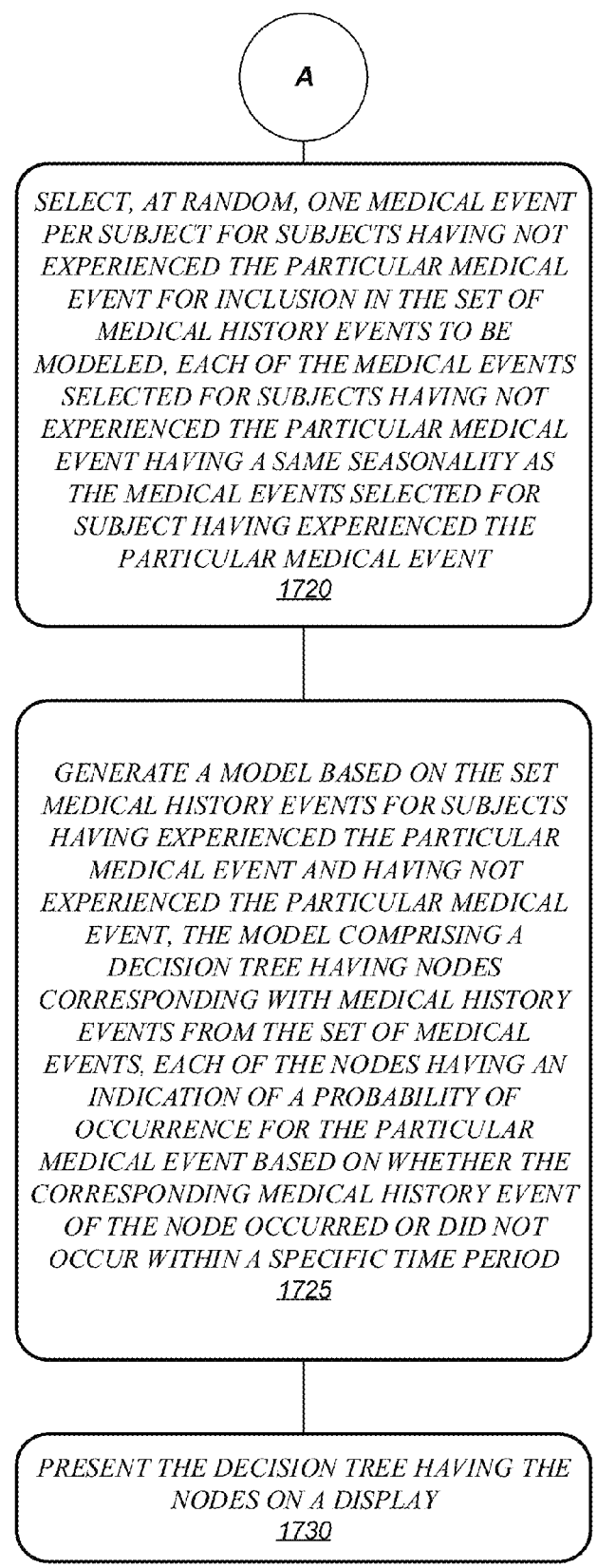

FIGS. 17A/17B illustrate an example of a logic flow diagram 1700. The logic flow 1700 may be representative of some or all of the operations executed by one or more embodiments described herein. For example, the logic flow 1700 may illustrate operations performed by the modeling system 1110, as discussed in FIGS. 11A-16B. In the illustrated embodiment shown in FIGS. 17A/17B, the logic flow 1700 may include obtaining medical event history information for subjects, the medical event history information comprising medical history events at block 1705. Further and at block 1710, the logic flow 1700 may include determining a particular medical event to determine a probability of occurrence based on a presence or absence of medical history events at specific prior time periods. The particular medical event may be obtained or determined in real-time or near real-time when a claim is filed that is associated with the event. In some instances, the particular medical event may be associated with a claim that has been previously filed. Further, the particular medical event may be chosen to determine whether a subject may experience, based on a probability of occurrence, the event at some future point in time. Embodiments are not limited in this manner.

At block 1715, the logic flow 1700 includes selecting, at random, one medical event per subject for subjects having experienced the particular medical event for inclusion in a set of medical history events to be modeled. Further and at block 1720, the logic flow 1700 includes selecting, at random, one medical event per subject for subjects having not experienced the particular medical event for inclusion in the set of medical history events to be modeled, each of the medical events selected for subjects having not experienced the particular medical event having a same seasonality as the medical events selected for subject having experienced the particular medical event. More specifically, events chosen for subjects who have not experienced the event modeled are chosen with a similar distribution (time/date wise) as the samples chosen from subjects who have experienced the event modeled. For example, if the event modeled is for a subject that took allergy medicine, the system will compare the history of subjects who took the allergy medicine with subjects who did not. Records chosen for subjects who did take an allergy medicine will tend to be from the fall and spring time periods. Thus, to have a corresponding set of subjects who did not take that allergy medicine, the system will choose records for each subject who did not take the allergy medicine having a similar distribution (e.g. from the spring and fall time periods).

The logic flow 1700, at block 1725, includes generating a model based on the set medical history events for subjects having experienced the particular medical event and having not experienced the particular medical event, the model comprising a decision tree data structure having decision tree nodes corresponding with medical history events from the set of medical events, each of the decision tree nodes having an indication of a probability of occurrence for the particular medical event based on whether the corresponding medical history event of the decision tree node occurred or did not occur within a specific time period. As previously discussed the model and decision tree may be used to detect fraudulent claims based on a likelihood or probability of occurrence for the particular medical history event modeled. Further and at block 1730, the logic flow 1700 may include presenting the decision tree having the decision tree nodes on a display. More specifically, a display of a display device may include presenting the decision tree and an indication of a probability of occurrence based on whether the subject experienced particular events are not, as illustrated in FIGS. 16A and 16B.

Some embodiments include a system, an apparatus, a device, and so forth having processing circuitry and logic. The logic at least partially implemented by the processing circuitry, and to obtain medical event history information for subjects, the medical event history information including the medical history events. The logic may also determine a particular medical event to determine a probability of occurrence based on a presence or absence of medical history events at specific prior time periods. Further, the logic may select, at random, one medical event per subject for subjects having experienced the particular medical event for inclusion in a set of medical history events to be modeled, and select, at random, one medical event per subject for subjects having not experienced the particular medical event for inclusion in the set of medical history events to be modeled, each of the medical events selected for subjects having not experienced the particular medical event having a same seasonality as the medical events selected for subject having experienced the particular medical event. In some instances, at least one of the medical history events of the set of medical history events is a different type of event than the particular medical event.

The logic may also generate a model based on the set medical history events for subjects having experienced the particular medical event and having not experienced the particular medical event, the model comprising a decision tree having nodes corresponding with medical history events from the set of medical events, each of the nodes having an indication of a probability of occurrence for the particular medical event based on whether the corresponding medical history event of the node occurred or did not occur within a specific time period. The logic also to present the decision tree having the nodes on a display.

In embodiments, the logic may also determine one or more category parameters associated with the particular medical event, the one or more category parameters comprising at least one of gender, age, and eligibility category and the model generated for the multiple category parameters, and select the medical events for the set medical history events for having the one or more category parameters associated with the particular medical event.

The system, apparatus, device, and so forth including the medical event history information comprising claim codes, subject identifiers, and medical history event dates for the subjects, and the logic to obtain mapping information comprising mappings of the claim codes to group claim code, and generate a reduce a number of medical history events by grouping two or more claim codes corresponding with a single medical history event into a group claim code based on the mapping information.

In embodiments, the logic to include a medical history event date for each of the medical history events in the set of medical history events, each medical history event date to indicate a date of last occurrence for the particular medical event or a null value for each subject having not experienced the particular medical history event.

The system, apparatus, device and so forth having the logic to determine occurrence indicators for each medical history event in the set of medical history events, each of the occurrence indicators to indicate whether a subject associated with the particular medical event experienced each medical history event, determine period indicators for each of the medical history events indicated as occurring to the subject by the occurrence indicators, each of the period indicators to indicate whether a medical history event occurred within a specified period of time The decision tree may also include decision branches coupling parent nodes with child nodes, each decision branch generated based on the occurrence indicators and the period indicators and indicate whether the subject associated with the particular medical event experienced or did not experience a medical history event of a parent node.

Embodiments discussed herein may also include the logic to generate the model and determine probability of occurrence for the particular medical event in real-time. Other embodiments include a computer-implemented method, and/or at least one non-transitory computer-readable storage medium having instructions that when executed cause processing circuitry to perform the various operations discussed herein.

These embodiments may provide technical advantages over previous systems by enabling a user of the system to interact with decision tree data structures to flag anomalies in real-time. The interactive system with the decision tree data structure allows a user to have a visual presentation and explanation of data anomalies that might ordinarily be hidden or difficult to locate, and may involve other types of data anomalies other than the medical or fraud examples described herein.

As discussed, some systems may use Hadoop®, an open-source framework for storing and analyzing big data in a distributed computing environment to generate models and probabilities of occurrence as discussed herein. Some systems may use cloud computing, which can enable ubiquitous, convenient, on-demand network access to a shared pool of configurable computing resources (e.g., networks, servers, storage, applications and services) that can be rapidly provisioned and released with minimal management effort or service provider interaction. Some grid systems may be implemented as a multi-node Hadoop® cluster, as understood by a person of skill in the art. Apache™ Hadoop® is an open-source software framework for distributed computing. Some systems may use the SAS® LASR™ Analytic Server in order to deliver statistical modeling and machine learning capabilities in a highly interactive programming environment, which may enable multiple users to concurrently manage data, transform variables, perform exploratory analysis, build and compare models and score with virtually no regards on the size of the data stored in Hadoop®. Some systems may use SAS In-Memory Statistics for Hadoop® to read big data once and analyze it several times by persisting it in-memory for the entire session.

What is claimed is:

1. An apparatus, comprising:
   processing circuitry; and
   logic, at least partially implemented by the processing circuitry, the logic to:
   obtain medical event history information for subjects, the medical event history information comprising medical history events;
   determine a particular medical event to determine a probability of occurrence based on a presence or absence of medical history events at specific prior time periods;
   select, at random, one medical event per subject for subjects having experienced the particular medical event for inclusion in a set of medical history events to be modeled;
   select, at random, one medical event per subject for subjects having not experienced the particular medical event for inclusion in the set of medical history events to be modeled, each of the medical events selected for subjects having not experienced the particular medical event having a same seasonality as the medical events selected for subject having experienced the particular medical event;
   generate a model based on the set medical history events for subjects having experienced the particular medical event and having not experienced the particular medical event, the model comprising a decision tree having nodes corresponding with medical history events from the set of medical events, each of the nodes having an indication of a probability of occurrence for the particular medical event based on whether the corresponding medical history event of the node occurred or did not occur within a specific time period; and
   present the decision tree having the nodes on a display.

2. The apparatus of claim 1, the particular medical event associated with multiple category parameters comprising at least one of gender, age, and eligibility category and the model generated for the multiple category parameters.

3. The apparatus of claim 1, the medical event history information comprising claim codes, subject identifiers, and medical history event dates for the subjects.

4. The apparatus of claim 1, the logic to reduce a number of medical history events by grouping two or more claim codes corresponding with a single medical history event into a group claim code.

5. The apparatus of claim 1, the logic to include a medical history event date for each of the medical history events in the set of medical history events, each medical history event date to indicate a date of last occurrence for the particular medical event or a null value for each subject having not experienced the particular medical history event.

6. The apparatus of claim 1, wherein at least one of the medical history events of the set of medical history events is a different type of event than the particular medical event.

7. The apparatus of claim 1, the logic to determine occurrence indicators for each medical history event in the set of medical history events, each of the occurrence indicators to indicate if a subject associated with the particular medical event experienced each medical history event.

8. The apparatus of claim 7, the logic to determine period indicators for each of the medical history events indicated as occurring to the subject by the occurrence indicators, each of the period indicators to indicate if a medical history event occurred within a specified period of time.

9. The apparatus of claim 8, the decision tree comprising decision branches coupling the nodes, each decision branch based on the occurrence indicators and the period indicators.

10. The apparatus of claim 1, the logic to generate the model and determine probability of occurrence for the particular medical event in real-time.

11. A computer-implemented method, comprising:
   obtaining medical event history information for subjects, the medical event history information comprising medical history events;
   determining a particular medical event to determine a probability of occurrence based on a presence or absence of medical history events at specific prior time periods;
   selecting, at random, one medical event per subject for subjects having experienced the particular medical event for inclusion in a set of medical events to be modeled;
   selecting, at random, one medical event per subject for subjects having not experienced the particular medical event for inclusion in the set of medical events to be modeled, each of the medical events selected for subjects having not experienced the particular medical event having a same seasonality as the medical events selected for subject having experienced the particular medical event;
   generating a model based on the set medical events for subjects having experienced the particular medical event and having not experienced the particular medical event, the model comprising a decision tree having nodes corresponding with medical history events from the set of medical events, each of the nodes having an indication of a probability of occurrence for the particular medical event based on whether the corresponding medical history event of the node occurred or did not occur within a specific time period; and presenting the decision tree having the nodes on a display.

12. The computer-implemented method of claim 11, the particular medical event associated with multiple category parameters comprising at least one of gender, age, and eligibility category and the model generated for the multiple category parameters.

13. The computer-implemented method of claim 11, the medical event history information comprising claim codes, subject identifiers, and medical history event dates for the subjects.

14. The computer-implemented method of claim 11, comprising reducing a number of medical history events by grouping two or more claim codes corresponding with a single medical history event into a group claim code.

15. The computer-implemented method of claim 11, comprising including a medical history event date for each of the medical history events in the set of medical history events, each medical history event date to indicate a date of last occurrence for the particular medical event or a null value for each subject having not experienced the particular medical history event.

16. The computer-implemented method of claim 11, wherein at least one of the medical history events of the set of medical events is a different type of event than the particular medical event.

17. The computer-implemented method of claim 11, comprising determining occurrence indicators for each medical history event in the set of medical events, each of the occurrence indicators to indicate if a subject associated with the particular medical event experienced each medical history event.

18. The computer-implemented method of claim 17, comprising determining period indicators for each of the medical history events indicated as occurring to the subject by the occurrence indicators, each of the period indicators to indicate if a medical history event occurred within a specified period of time.

19. The computer-implemented method of claim 18, the decision tree comprising decision branches coupling the nodes, each decision branch based on the occurrence indicators and the period indicators.

20. The computer-implemented method of claim 11, comprising generating the model and determine probability of occurrence for the particular medical event in real-time.

21. At least one non-transitory computer-readable storage medium comprising instructions that when executed cause processing circuitry to:

obtain medical event history information for subjects, the medical event history information comprising medical history events;

determine a particular medical event to determine a probability of occurrence based on a presence or absence of medical history events at specific prior time periods;

select, at random, one medical event per subject for subjects having experienced the particular medical event for inclusion in a set of medical history events to be modeled;

select, at random, one medical event per subject for subjects having not experienced the particular medical event for inclusion in the set of medical history events to be modeled, each of the medical events selected for subjects having not experienced the particular medical event having a same seasonality as the medical events selected for subject having experienced the particular medical event;

generate a model based on the set medical history events for subjects having experienced the particular medical event and having not experienced the particular medical event, the model comprising a decision tree having nodes corresponding with medical history events from the set of medical history events, each of the nodes having an indication of a probability of occurrence for the particular medical event based on whether the corresponding medical history event of the node occurred or did not occur within a specific time period; and present the decision tree having the nodes on a display.

22. The non-transitory computer-readable storage medium of claim 21, the particular medical event associated with multiple category parameters comprising at least one of gender, age, and eligibility category and the model generated for the multiple category parameters.

23. The non-transitory computer-readable storage medium of claim 21, the medical event history information comprising claim codes, subject identifiers, and medical history event dates for the subjects.

24. The non-transitory computer-readable storage medium of claim 21, comprising instructions that when executed cause the processing circuitry to reduce a number of medical history events by grouping two or more claim codes corresponding with a single medical history event into a group claim code.

25. The non-transitory computer-readable storage medium of claim 21, comprising instructions that when executed cause the processing circuitry to include a medical history event date for each of the medical history events in the set of medical history events, each medical history event date to indicate a date of last occurrence for the particular medical event or a null value for each subject having not experienced the particular medical event.

26. The non-transitory computer-readable storage medium of claim 21, wherein at least one of the medical history events of the set of medical history events is a different type of event than the particular medical event.

27. The non-transitory computer-readable storage medium of claim 21, comprising instructions that when executed cause the processing circuitry to determine occurrence indicators for each medical history event in the set of medical history events, each of the occurrence indicators to indicate if a subject associated with the particular medical event experienced each medical history event.

28. The non-transitory computer-readable storage medium of claim 27, comprising instructions that when executed cause the processing circuitry to determine period indicators for each of the medical history events indicated as occurring to the subject by the occurrence indicators, each of the period indicators to indicate if a medical history event occurred within a specified period of time.

29. The non-transitory computer-readable storage medium of claim 28, the decision tree comprising decision branches coupling the nodes, each decision branch based on the occurrence indicators and the period indicators.

30. The non-transitory computer-readable storage medium of claim 21, comprising instructions that when executed cause the processing circuitry to generate the model and determine probability of occurrence for the particular medical event in real-time.

\* \* \* \* \*